US012723269B2

(12) United States Patent
Um et al.

(10) Patent No.: US 12,723,269 B2
(45) Date of Patent: Sep. 1, 2026

(54) METHOD FOR PRODUCING CARBON COMPOUND OF ACETOGEN STRAIN THROUGH SEMI-MIXOTROPHIC FERMENTATION SUPPLEMENTED ABSORBENT RESIN

(71) Applicant: KOREA INSTITUTE OF SCIENCE AND TECHNOLOGY, Seoul (KR)

(72) Inventors: Youngsoon Um, Seoul (KR); Deurim Yun, Seoul (KR); Sun Mi Lee, Seoul (KR); Gyeongtaek Gong, Seoul (KR); Ja Kyong Ko, Seoul (KR); Jung Ho Ahn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 414 days.

(21) Appl. No.: 18/470,284

(22) Filed: Sep. 19, 2023

(65) Prior Publication Data

US 2024/0117389 A1 Apr. 11, 2024

(30) Foreign Application Priority Data

Oct. 7, 2022 (KR) ........................ 10-2022-0128700

(51) Int. Cl.

| | |
|---|---|
| ***C12P 7/40*** | (2006.01) |
| ***C12P 7/02*** | (2006.01) |
| ***C12P 7/16*** | (2006.01) |
| ***C12P 7/52*** | (2006.01) |

(52) U.S. Cl.

CPC .................. *C12P 7/40* (2013.01); *C12P 7/02* (2013.01); *C12P 7/16* (2013.01); *C12P 7/52* (2013.01)

(58) Field of Classification Search

CPC ...... C12P 7/40; C12P 7/02; C12P 7/16; C12P 7/52; C12P 7/065; C12P 7/54; C12P 7/04; Y02E 50/10

See application file for complete search history.

(56) References Cited

U.S. PATENT DOCUMENTS

| | | | |
|---|---|---|---|
| 9,938,542 B2 * | 4/2018 | Tracy ........................ | C12P 7/18 |
| 10,975,448 B2 | 4/2021 | Um et al. | |
| 2016/0251683 A1 | 9/2016 | Tracy et al. | |
| 2019/0390158 A1 | 12/2019 | Dyson et al. | |

FOREIGN PATENT DOCUMENTS

| | | |
|---|---|---|
| JP | 2010-515441 A | 5/2010 |
| JP | 6680671 B2 | 4/2020 |
| KR | 10-1316732 B1 | 10/2013 |
| KR | 10-1985307 B1 | 6/2019 |
| WO | 2008/086811 A1 | 7/2008 |

OTHER PUBLICATIONS

Nielsen et al., Predicting the adsorption of second generation biofuels by polymeric resins with applications for in situ product recovery (ISPR). Bioresource Technol., 2010, vol. 10: 2762-2769. (Year: 2010).*

Raganati et al., Bio-butanol separation by adsorption on various materials: Assessment of isotherms and effects of other ABE-fermentation compounds. Separat. Purification. Technol., 2018, vol. 191: 328-339 (Year: 2018).*

Written Decision on Registration for Korea Patent Application No. 10-2022-0128700, dated Apr. 28, 2025.

* cited by examiner

*Primary Examiner* — Ganapathirama Raghu

(57) ABSTRACT

The present disclosure is to provide a method capable of producing an organic acid in high yield from an acetic acid strain using synthesis gas as a substrate. According to the present disclosure, the productivity of metabolites with C2 to C6 carbon atoms derived from synthesis gas and the selectivity of hexanoic acid production among metabolites can be improved through a first fermentation step of simultaneously providing a substrate comprising synthesis gas and sugar; and a second fermentation step of semi-mixotrophic fermentation of providing only the substrate comprising the synthesis gas. Therefore, the disclosure can contribute to sustainable chemical production using synthesis gas.

8 Claims, 22 Drawing Sheets

METHOD FOR PRODUCING CARBON COMPOUND OF ACETOGEN STRAIN THROUGH SEMI-MIXOTROPHIC FERMENTATION SUPPLEMENTED ABSORBENT RESIN

DESCRIPTION OF GOVERNMENT-SPONSORED RESEARCH

This study was conducted by the following national project.

- Ministry Name: Ministry of Strategy and Finance; Project management (specialized) institute name: National Research Foundation; Research program title: Climate change mitigation technology development; Research project title: development of strains and bioprocesses that produce medium-chain/long-chain fatty acids by converting unused biomass; Project number: 2020M1A2A2080847, Project assignment number: 1711158983
- Ministry Name: Ministry of Strategy and Finance; Project management (specialized) institute name: National Research Foundation; Research program title: biomass-based carbon-neutral bioplastic product technology development; Research project title: 100% biomass-based bioplasticizer production technology development to replace petroleum-based plasticizers; Project number: 2022M3J4A1052750, Project assignment number: 1055000966

CROSS REFERENCE TO RELATED APPLICATION

The present application claims priority to Korean Patent Application No. 10-2022-0128700, filed Oct. 7, 2022, the entire contents of which is incorporated herein for all purposes by this reference.

BACKGROUND OF THE INVENTION

Field of the Invention

The specification relates to a method for producing carbon compound using acetogen strain.

Description of the Related Art

Organic acids are useful compounds that can be used in aviation fuel and flavoring materials and are important components that affect the metabolism of intestinal microbes. Organic acids are classified according to the hydrocarbon chain length. Hexanoic acid, a medium-chain fatty acid, is a useful compound that can be used as a precursor for hexanol, which is a substitute for food additives, perfumes, and gasoline. Acetogen strains are strains capable of producing acetic acid as a metabolite from carbon atom-based gases such as carbon monoxide and carbon dioxide, and research is being conducted to produce organic acids such as fatty acids using synthesis gas contained in greenhouse gases, industrial by-product gases, etc. as a substrate using acetogen strains.

However, in the case of a typical production method using an acetogen strain, the utilization rate of carbon monoxide in synthesis gas is low, which inhibits growth, and the production efficiency of organic acids such as hexanoic acid is low due to low ATP production and low cell mass. In addition, chain extension from acetyl-CoA to hexanoyl-CoA has a problem in that a lot of reducing power is required to generate hexanoic acid.

SUMMARY OF THE INVENTION

The problem to be solved by the present disclosure is to provide a method capable of producing organic acids in high yield from acetic acid strains using synthesis gas as a substrate.

In order to solve the above problems, one embodiment of the present disclosure provides a method for producing a metabolite using an acetogen strain, comprising:

- a first fermentation step of fermenting an acetogen strain in a medium comprising synthesis gas and sugar;
- a second fermentation step of further fermenting the cultured acetogen strain by supplying the synthesis gas in the same medium after all the sugars are consumed in the first fermentation step,
- wherein the medium further comprises an adsorption resin of a metabolite, and the metabolite comprises a carbon number of C2 to C6.

The method according to one embodiment of the present disclosure can improve the productivity of metabolites with C2 to C6 carbon atoms derived from synthesis gas through a first fermentation step of simultaneously providing a substrate comprising synthesis gas and sugar; and a second fermentation step of semi-mixotrophic fermentation of providing only the substrate comprising the synthesis gas. In addition, the selectivity of hexanoic acid production among the metabolites comprising C2 to C6 carbon atoms can be improved by removing the metabolites produced through the adsorption resin during fermentation.

DETAILED DESCRIPTION OF THE INVENTION

Figure 1A:
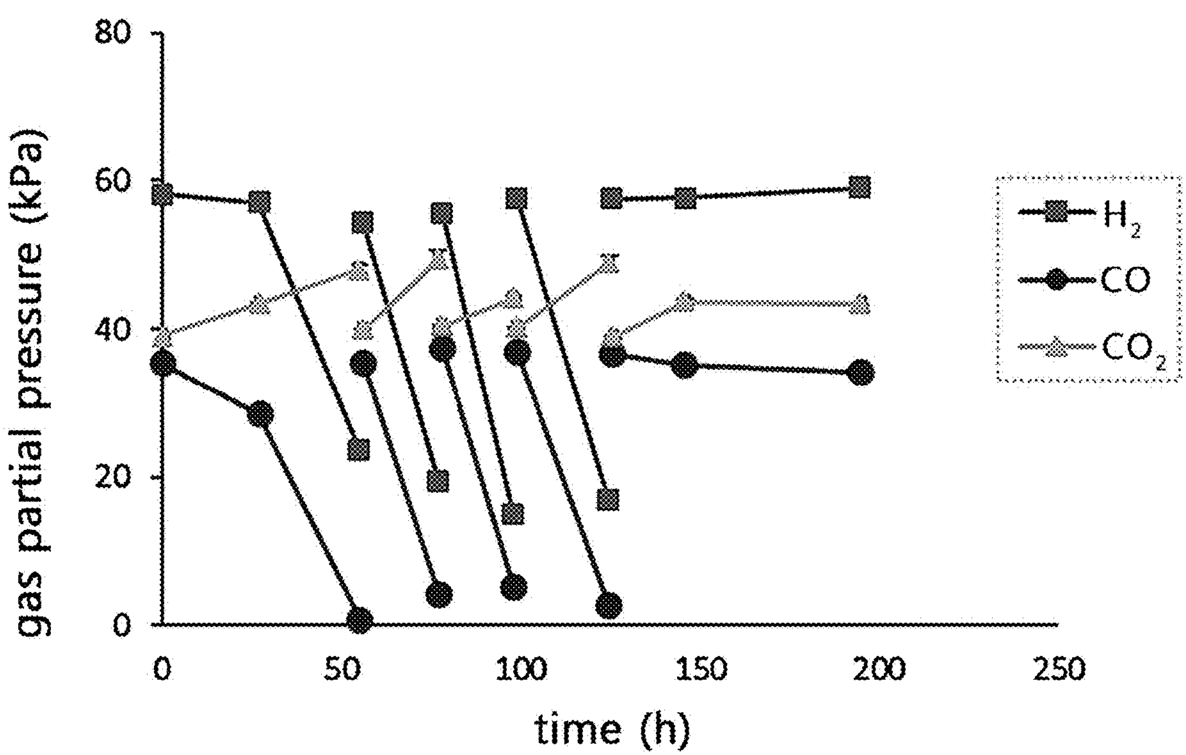
FIG. 1A is a diagram showing an analysis of a synthesis gas consumption tendency during autotrophic fermentation of an acetogen strain as Comparative Example of the present disclosure.

Hereinafter, preferred embodiments of the present disclosure will be described in detail with reference to the accompanying drawings.

Embodiments of the present disclosure disclosed in the application are illustrated for purposes of explanation only, and the embodiments of the present disclosure may be implemented in various forms and should not be construed as being limited to the embodiments described in the application. Since the present disclosure may be subject to various changes and may have various forms, the embodiments are not intended to limit the present disclosure to a specific disclosure form, and it should be understood to include all modifications, equivalents and substitutes included in the spirit and scope of the present disclosure. The singular forms are intended to include the plural forms as well, unless the context clearly indicates otherwise. It will be further understood that the terms “comprises,” “includes,” “contains,” or “has,” when used in this application, specify the presence of stated features, integers, steps, operations, elements, components, or combinations thereof, but do not preclude the presence or addition of one or more other features, integers, steps, operations, elements, components, or combinations thereof.

One embodiment of the present disclosure may provide a method for producing a metabolite using an acetogen strain, comprising:

a first fermentation step of fermenting an acetogen strain in a medium comprising synthesis gas and sugar;

a second fermentation step of further fermenting the cultured acetogen strain by supplying the synthesis gas in the same medium after all the sugars are consumed in the first fermentation step, wherein the medium further comprises an adsorption resin of a metabolite, and the metabolite comprises a carbon number of C2 to C6.

In the present specification, the term “acetogen strain” refers to a strain capable of biologically converting acetly-CoA, a precursor of various substances such as ethanol, acetic acid, butyric acid, butanol, using a carbon atom (C1)-based gas such as carbon dioxide or carbon monoxide contained in greenhouse gases or waste gases generated in the combustion process of coal, etc. through the Wood-Ljungdahl pathway.

In one embodiment, the acetogen strain of the present disclosure is not limited in its type, but may comprise, for example, a *Clostridium* sp. strain. As one embodiment, the *Clostridium* sp. strain may comprise one or more species selected from the group consisting of *Clostridium* sp. JS66 strain (accession number: KCTC13355BP, deposit date: Sep. 19, 2017), *Clostridium carboxidivorans* P7 (ATCC BAA-624), and the like.

The *Clostridium* sp. J566 strain can produce hexanol and hexanoic acid, which are compounds with 6 carbon atoms, whereas most acetogen strains can produce compounds with 2 carbon atoms such as acetic acid as final metabolites. However, the production of hexanoic acid by *Clostridium* sp. J566 strain is very low, making it difficult to use it industrially. In addition, there is a limit in that almost no synthesis gas is consumed during glucose fermentation. However, according to one embodiment of the present disclosure, the production yield of hexanoic acid can be remarkably increased by using the *Clostridium* sp. J566 strain while increasing the consumption of synthesis gas and the production concentration of hexanoic acid.

In this specification, the term "semi-mixotrophic fermentation" means comprising all the steps of initiating mixotrophic fermentation by adding synthesis gas and sugar in the first stage of fermentation, and conducting autotrophic fermentation of fed-batch culture in the second stage of fermentation in which only synthesis gas is injected into the same medium after all sugar is consumed. Therefore, the semi-mixotrophic fermentation means a fermentation method comprising a first fermentation step (mixotrophic fermentation step) in which a strain is fermented in a medium comprising synthesis gas and sugar, and a second fermentation step (autotrophic fermentation) in which sugar is not supplied to the cultured strain and culture medium in the mixotrophic fermentation step, and only synthesis gas is supplied for fermentation. The semi-mixotrophic fermentation of the present disclosure is distinguished from individual fermentation consisting only of heterotrophic fermentation (glucose fermentation) step or autotrophic fermentation in that it further comprises the second fermentation step after the mixotrophic fermentation step. The semi-mixotrophic fermentation method according to one embodiment increases the initial cell amount through the first fermentation step, and then injects only synthesis gas in the second fermentation step to perform autotrophic fermentation, so that the productivity of organic acids such as hexanoic acid can be increased by maximizing synthesis gas consumption due to the increased cell mass caused by the initial consumption of carbon sources such as glucose.

In addition, the present disclosure, as one embodiment, adds an adsorption resin to the medium in the fermentation initiation step to remove the hexanoic acid produced by the acetogen strain, so that the hexanoic acid itself produced can be prevented from causing inhibition of hexanoic acid production due to cell membrane structural modification and pH reduction of acetogen strains.

In one embodiment, the synthesis gas comprised in each medium of the first fermentation step and the second fermentation step may comprise one or more of carbon monoxide (CO), carbon dioxide ($CO_2$) and hydrogen ($H_2$). Specifically, the synthesis gas may comprise one or more of carbon monoxide (CO), carbon dioxide ($CO_2$) and hydrogen ($H_2$). More specifically, the synthesis gas may comprise 10 pressure % or more, 15 pressure % or more, 20 pressure % or more, 25 pressure % or more, 30 pressure % or more, 35 pressure % or more, 40 pressure % or more, 45 pressure % or more, 50 pressure % or more, 55 pressure % or more, 60 pressure % or more, or 65 pressure % or more of carbon monoxide based on the total pressure of the synthesis gas. The synthesis gas may comprise 100 pressure % or less, 90 pressure % or less, 80 pressure % or less, 70 pressure % or less, 65 pressure % or less, 60 pressure % or less, 55 pressure % or less, 50 pressure % or less, 45 pressure % or less, 40 pressure % or less, 35 pressure % or less, 30 pressure % or less, 25 pressure % or less, 20 pressure % or less or 15 pressure % or less of carbon monoxide based on the total pressure of the synthesis gas. As one embodiment, in view of increasing the productivity of hexanoic acid, the present disclosure may comprise 40 to 70 pressure %, more specifically, 50 to 70 pressure % of carbon monoxide, based on the total pressure of synthesis gas. According to the method according to one embodiment of the present disclosure, hexanoic acid can be produced using low-cost synthesis gas, which is an industrial waste. In addition, the acetic acid produced by increasing the carbon monoxide ratio in the supplied synthesis gas is converted to hexanoic acid, thereby increasing the selectivity of the production of hexanoic acid.

As one embodiment, the sugar comprised in the medium of the first fermentation step may comprise one or more of glucose, sucrose, fructose, galactose, xylose, arabinose, mannose, cellobiose, and sucreose, but is not limited thereto.

As one embodiment, the concentration of the sugar is not limited, and may be comprised, for example, at a concentration of 1 g/L or more, 2 g/L or more, 3 g/L or more, 4 g/L or more, or 5 g/L or more based on the total volume of the medium. Specifically, the sugar may be comprised at a concentration of 5 g/L based on the total volume of the medium.

As one embodiment, the pH of each of the first fermentation step and the second fermentation step may be 5 to 8. Specifically, the pH of each step may be 5 or more, 5.5 or more, 6 or more, or 7 or more, and may be 8 or less, 7 or less, 6.5 or less, or 6 or less.

As one embodiment, the culture temperature of each of the first fermentation step and the second fermentation step is not limited and may vary depending on the type of strain. For example, the incubation temperature of each step may be 25 to 37° C., respectively. Specifically, the culture temperature of each step may be 25° C. or greater, 26° C. or greater, 27° C. or greater, 28° C. or greater, 29° C. or greater, 30° C. or greater, 31° C. or greater, 32° C. or greater, 33° C. or greater, 34° C. or greater, or 35° C. or greater, and may be 37° C. or less, 36° C. or less, 35° C. or less, 34° C. or less, 33° C. or less, 32° C. or less, 31° C. or less, 30° C. or less, 29° C. or less, 28° C. or less, 27° C. or less, or 26° C. or less.

As one embodiment, each of the first fermentation step and the second fermentation step may be carried out under anaerobic conditions. As used herein, the term "anaerobic condition" refers to an environment in which the amount of oxygen is small to an extent that an obligate anaerobic microorganism can survive or oxygen is not present.

In one embodiment, each of the first fermentation step and the second fermentation step may be performed under the condition that the initial total gas pressure of mixed gas is 0.5 to 2.5 bar, but is not limited thereto. Specifically, the initial total gas pressure of the mixed gas in each step may be 0.5 bar or more, 0.7 bar or more, 0.9 bar or more, 1 bar or more, 1.2 bar or more, 1.3 bar or more, 1.4 bar or more, 1.5 bar or more, 1.7 bar or more, or 2 bar or more, and may be 3 bar or less, 2.8 bar or less, 2.5 bar or less, 2.2 bar or less, 2 bar or less, 1.8 bar or less, 1.7 bar or less, 1.6 bar or less, 1.5 bar or less, 1.2 bar or less, or 1 bar or less.

As one embodiment, the medium of the first fermentation step and the second fermentation step may each further comprise a yeast extract. For example, the medium may further comprise a yeast extract in an amount of 0.1 g/L to 10 g/L, for example, 0.5 g/L to 2 g/L.

As one embodiment, the first fermentation step may be conducted for 10 to 20 hours. Specifically, the first fermentation step may be conducted for 10 hours or more, 11 hours or more, 12 hours or more, 13 hours or more, 14 hours or more, 15 hours or more, 16 hours or more, 17 hours or more, 18 hours or more, or 19 hours or more, and may be conducted for 20 hours or less, 19 hours or less, 18 hours or less, 17 hours or less, 16 hours or less, 15 hours or less, 14 hours or less, 13 hours or less, 12 hours or less, or 11 hours or less. As one embodiment, the first fermentation step may be conducted until the acetogen strain consumes all of the sugars in the medium.

As one embodiment, the second fermentation step may be conducted for 100 to 500 hours. Specifically, the second fermentation step may be conducted for 100 hours or more, 150 hours or more, 200 hours or more, 250 hours or more, 300 hours or more, 350 hours or more, 400 hours or more, or 450 hours or more, and may be conducted for 500 hours or less, 450 hours or less, 400 hours or less, 350 hours or less, 300 hours or less, 250 hours or less, 200 hours or less, or 150 hours or less. As one embodiment, the second fermentation step may be conducted until synthesis gas is no longer consumed or the acetogen strain no longer produces metabolites.

As one embodiment, the adsorption resin is not limited as long as it can adsorb metabolites, and may comprise porous polymer particles. Specifically, the porous polymer particles may be capable of adsorbing substances having a molecular weight of 100 to 1000. Specifically, the porous polymer particles may comprise porous aromatic polymer particles. For example, the porous aromatic-based polymer particles may be porous polystyrene-based polymer particles.

Specifically, the porous polymer particles may satisfy one or more of the followings: a specific surface area of 700 to 1500 m 2/g; a pore radius of 40 to 85 Å; a particle size range of 200 to 1500 μm; and a pore volume of 0.8 to 1.8 ml/g.

As one embodiment, the specific surface area may be 1100 to 1500 m 2/g.

As one embodiment, the pore radius may be 45 to 55 Å.

As one embodiment, the particle size range of the particles may be 250 to 700 μm.

As one embodiment, the pore volume may be 1.2 to 1.6 ml/g.

As one embodiment, the adsorption resin may comprise at least one selected from the group consisting of TRILITE® GSH-20 (manufacturer: Samyang Corporation) and TRILITE® GSP-25 (manufacturer: Samyang Corporation).

One embodiment of the present disclosure can easily recover metabolites produced in the medium by using the adsorption resin as described above for adsorption and removal of metabolites. In addition, by facilitating the movement of synthesis gas in the medium during the fermentation step, when an organic solvent or the like is used, it is possible to solve the problem that the organic solvent rises on the medium and the movement of the synthesis gas is inhibited so that it cannot be used as a substrate.

As one embodiment, the method may further comprise recovering the metabolites from the adsorption resin after the fermentation is completed.

The metabolite produced according to the method of the present disclosure may be a compound having a carbon number of C2 to C6 or an alcohol having a carbon number of C2 to C6, and the specific type of the metabolite may vary depending on the type of acetogen strain used in the method and/or the type of substrate used for culturing. For example, the metabolite may comprise one or more of acetic acid, butyric acid, hexanoic acid, ethanol, butanol and hexanol. More specifically, the metabolite may comprise one or more of hexanoic acid ($C_6H_{11}COOH$), hexanol ($C_6H_{13}OH$), butyric acid ($C_4H_8O_2$) and butanol ($C_4H_9OH$).

As one embodiment, the method may improve the production yield of hexanoic acid and/or hexanol among metabolites. For example, the method may be a method of producing the hexanoic acid by converting 25 mol % or more of a total carbon mole (C mol) of the consumed carbon source to a carbon mole (C mol) of the hexanoic acid.

Hereinafter, the present invention will be described in more detail with reference to Examples of the present invention. However, it will be apparent to those skilled in the art that the following Examples are provided for illustrative purposes only to describe the present invention more specifically, and the scope of the present invention is not limited thereto.

Comparative Example 1

As Comparative Example of the present disclosure, autotrophic fermentation was conducted in a medium comprising only synthesis gas as a carbon and an energy source using an acetogen strain to analyze synthesis gas consumption and metabolite productivity. As an acetogen strain, *Clostridium* sp. JS66 was used.

The composition of the medium comprised 1 g yeast extract, 2 g ammonium chloride ($NH_4C_1$), 0.08 g calcium chloride ($CaCl_2 \cdot 2H_2O$), 0.4 g magnesium sulfate ($MgSO_4 \cdot 7H_2O$), 0.2 g potassium chloride (KCl), 0.2 g potassium phosphate ($KH_2PO_4$), 0.01 g manganese sulfate ($MnSO_4 \cdot H_2O$), 0.002 g sodium molybdate ($NaMoO_4 \cdot 2H_2O$), 0.2 g cysteine, and trace elements, per liter of total volume. The trace element composition is shown in Table 1 below.

TABLE 1

| Trace elements | mg/L |
|---|---|
| Nitrilotriacetic acid | 20 |
| $MnSO_4 \cdot H_2O$ | 10 |
| $Fe(SO_4)_2(NH_4)_2 \cdot 6H_2O$ | 8 |
| $CoC1_2 \cdot 6H_2O$ | 2 |
| $ZnSO_4 \cdot 7H_2O$ | 0.002 |
| $CuC1_2 \cdot 2H_2O$ | 0.2 |
| $NiC1_2 \cdot 2H_2O$ | 0.2 |
| $Na_2MoO_4 \cdot 2H_20$ | 0.2 |
| $Na_2WO_4$ | 0.2 |
| $KAI(SO_4)_2 \cdot 12H_2O$ | 0.2 |
| $H_3BO_3$ | 0.1 |

During fermentation, 50 mM 2-[N-morpholino]ethanesulfonic acid (MES) was added for pH buffering, and the initial pH of the medium was adjusted to 6 using 2 M potassium hydroxide (KOH).

During the autotrophic fermentation, with fed-batch culture, 20 ml of the medium was put in a 157 ml serum bottle, and *Clostridium* sp. JS66 was inoculated as an acetogen strain, and then synthesis gas was supplied at 1.25 bar. In this case, as the synthesis gas, carbon monoxide (CO), carbon dioxide ($CO_2$), and hydrogen ($H_2$) were injected at a ratio of 3:3:4, respectively. It was cultured at a rotational speed of 100 rpm at a temperature of 30° C. in a shaking incubator, and gas consumption, pH change and production substances were analyzed over time. The culture was terminated when synthesis gas consumption ceased.

The gas partial pressures of carbon monoxide, carbon dioxide, and hydrogen were analyzed using a gas chromatography (Agilent Technologies 6890N, CA, USA) equipped with a thermal conductivity detector (TCD). The column was a Porepack Q, the inlet temperature was 100° C., the detector temperature was 200° C., and the mobile gas argon was 15.5 mL/min at 50° C. Ethanol, butanol, hexanol, acetic acid (AA), butyric acid (BA) and hexanoic acid (HA) were analyzed using a gas chromatography (Agilent Technologies 6890N, CA, USA) equipped with a flame ionization detector (FID). For the column, HP-Innowax (agilent, 30 m×0.32 mm×0.25 μm) was used, and the inlet temperature was maintained at 250° C. and the detector temperature was maintained at 250° C. The oven temperature was increased from an initial 50° C. to a final temperature of 250° C. by increasing by 10° C./min. Helium gas was used as the moving gas and the inlet pressure was maintained at 9.41 psi. Glucose was analyzed using liquid chromatography (Agilent Technologies 1260 Infinity, CA, USA) equipped with a RID detector. The column used was a HI-PLEX H (300×7.7 mm) column, the column temperature was 65° C., and 5 mM sulfuric acid was flowed at 0.6 mL/min as a mobile phase.

Figure 1B:
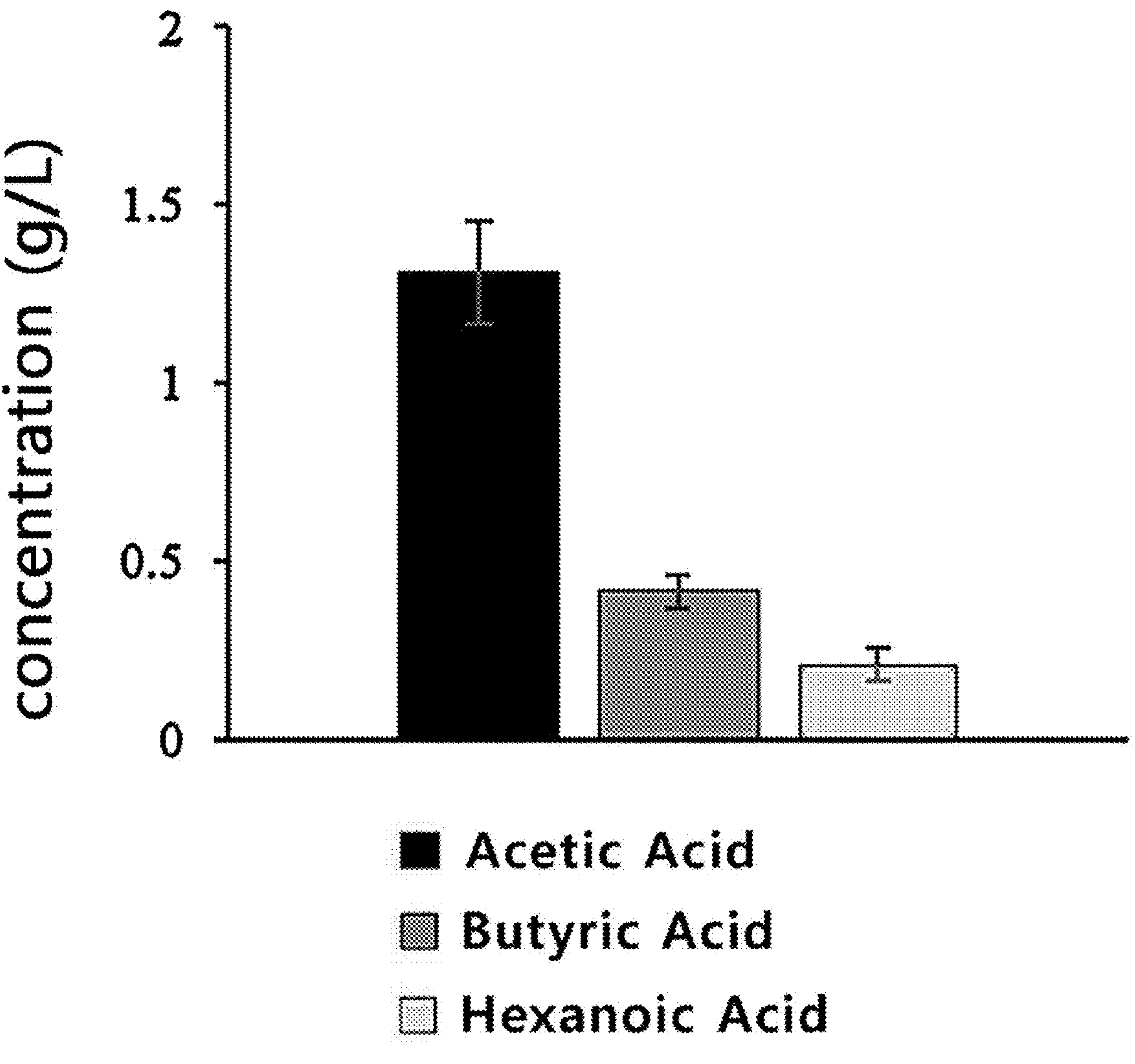
FIG. 1B is a diagram showing a final metabolite concentration analyzed during autotrophic fermentation of an acetogen strain as Comparative Example of the present disclosure.

As a result, as shown in FIG. 1A, the strain consumed synthesis gas for 150 hours during autotrophic fermentation, and the total gas consumption was 8.05 mmol of hydrogen and 7.17 mmol of carbon monoxide. As shown in FIG. 1B, the concentration of metabolites was less than 1 g/L except for acetic acid, and 1.31 g/L of acetic acid was produced. This means that in the autotrophic fermentation, most metabolites are produced as acetic acid due to low cell mass and ATP.

Comparative Example 2

As Comparative Example of the present disclosure in which the semi-mixotrophic fermentation method of an embodiment of the present disclosure was carried out under the condition of no absorbent resin, the synthesis gas consumption and metabolite productivity of acetogen strains were analyzed according to the following method.

An additional 5 g/L of glucose was added to the same medium composition as in Comparative Example 1, 20 ml of medium was placed in a 157 ml serum bottle, microorganisms were inoculated, and synthesis gas was supplied at 1.25 bar. Synthesis gas was injected with carbon monoxide (CO), carbon dioxide ($CO_2$), and hydrogen ($H_2$) at a ratio of 3:3:4, respectively. It was cultured at a rotational speed of 100 rpm at a temperature of 30° C. in a shaking incubator. The sugar in the medium was consumed within 24 hours, and even after the sugar was consumed, synthesis gas was continuously injected into the fed-batch culture and further fermented for 430 hours, and the final fermentation time was 454 hours.

Gas consumption, pH change, and produced materials over time were analyzed in the same manner as in Comparative Example 1.

Figure 2A:
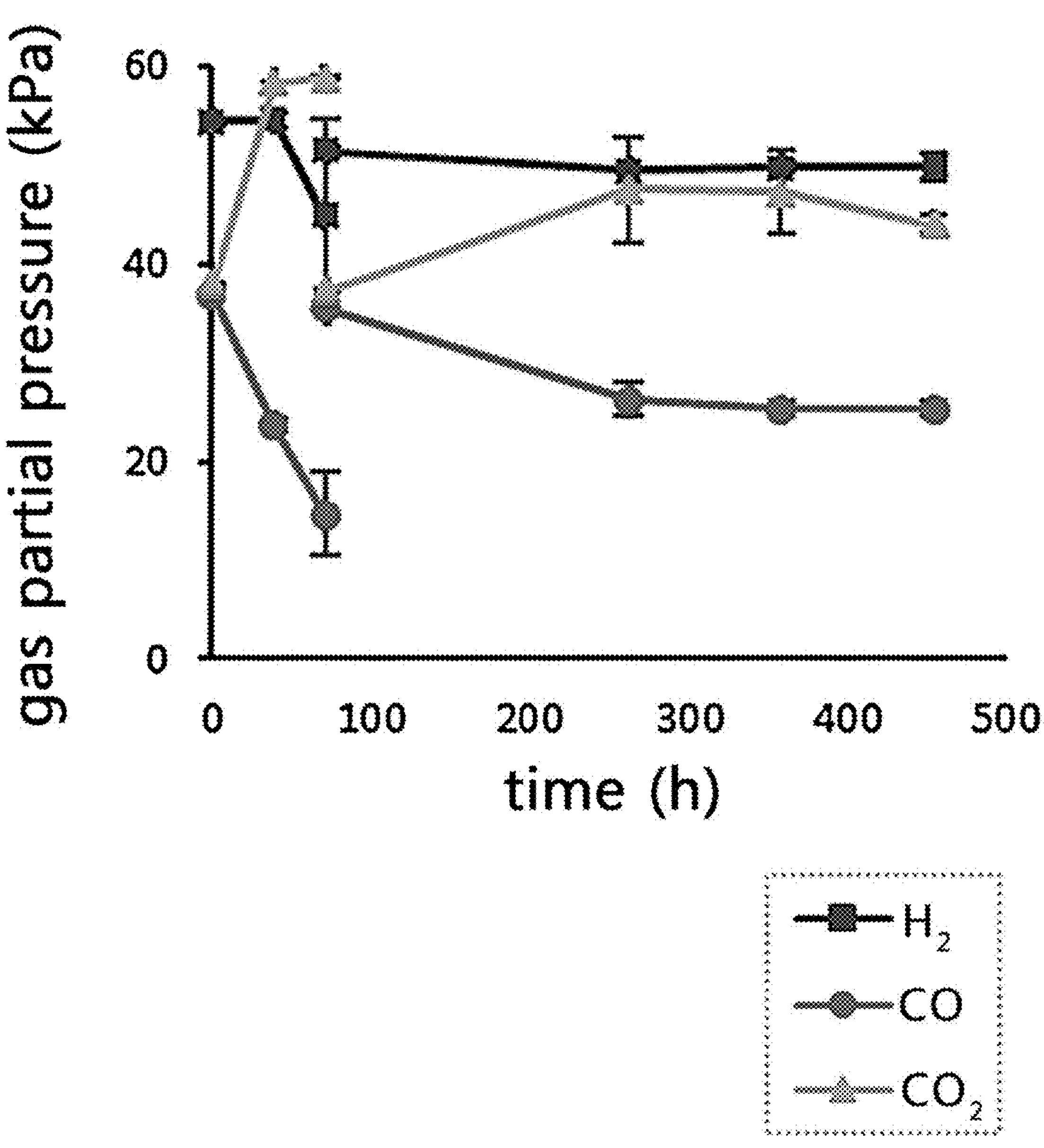
FIG. 2A is a diagram showing an analysis of a synthesis gas consumption during semi-mixotrophic fermentation without adsorption resin of an acetogen strain as Comparative Example of the present disclosure.
Figure 2B:
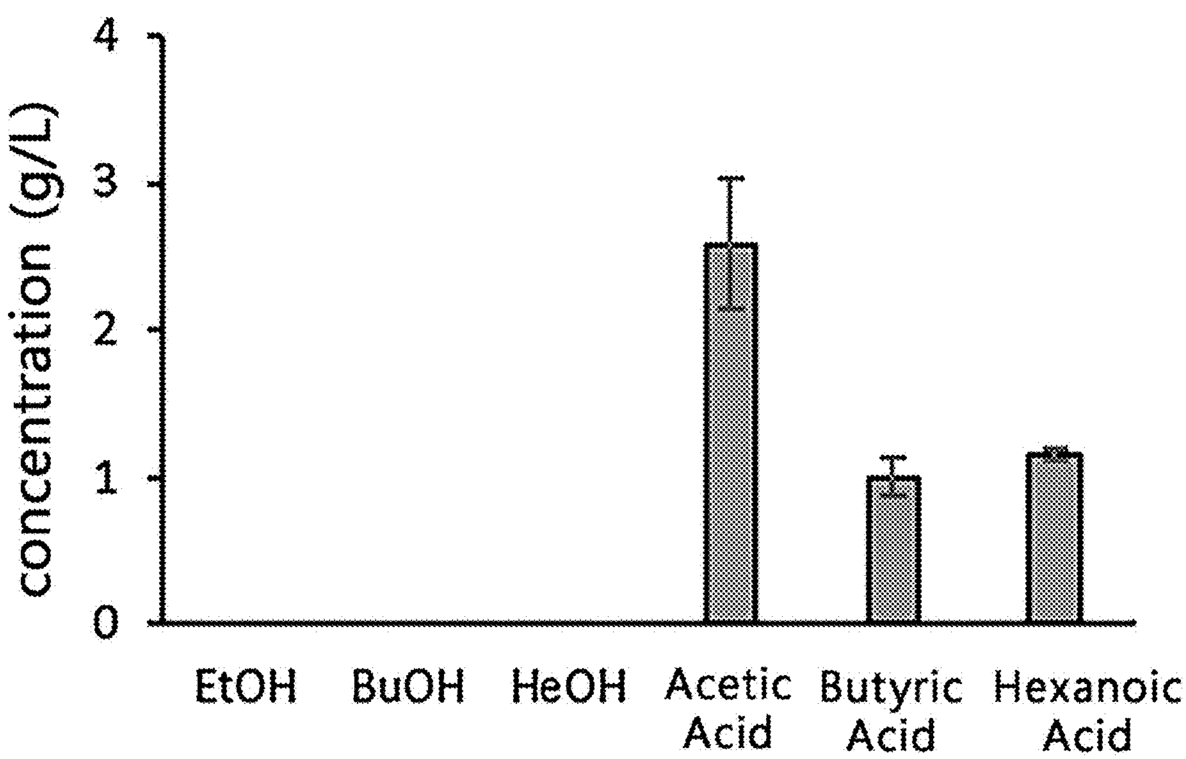
FIG. 2B is a diagram showing an analysis of a final metabolite concentration during semi-mixotrophic fermentation without an adsorption resin of an acetogen strain as Comparative Example of the present disclosure.
Figure 2C:
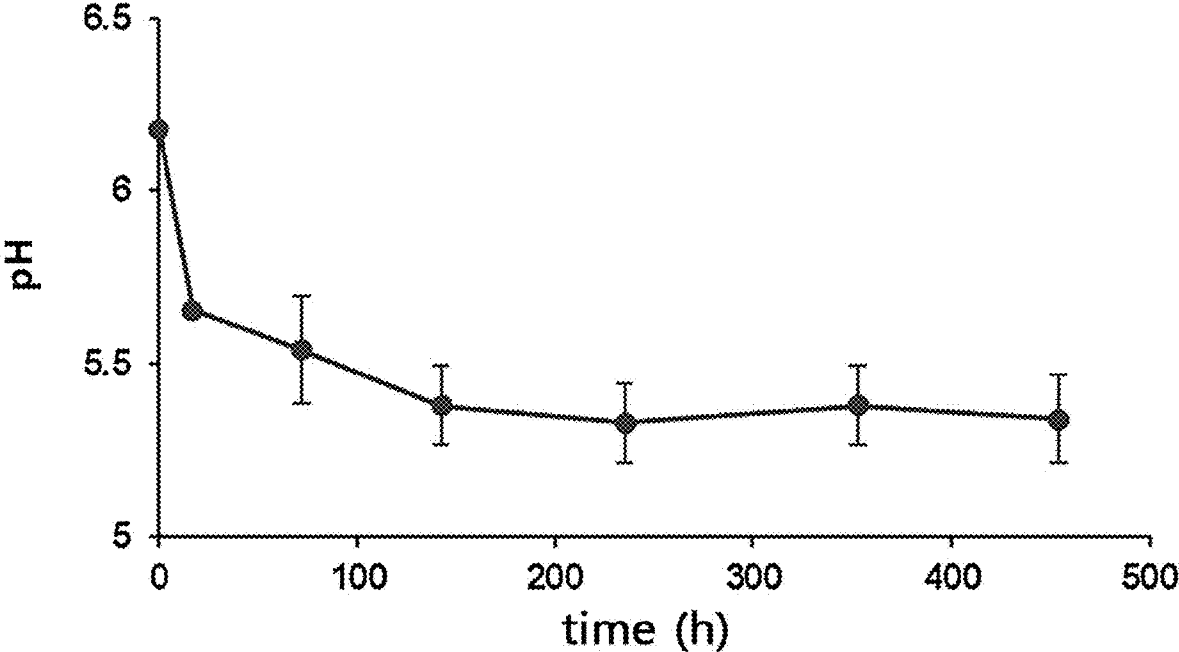
FIG. 2C is a diagram showing an analysis of pH change according to a fermentation time of an acetogen strain in Comparative Example of the present disclosure.

As a result, as shown in FIGS. 2A and 2B, the acetogen strain consumed 5 g/L of glucose within 24 hours, and the consumption of the synthesis gas stopped before 100 hours, resulting in a total gas consumption of 0.58 mmol of hydrogen and 1.75 mmol of carbon monoxide. FIG. 2C shows the analysis of pH change over time. The pH was initially 6.17, decreased to 5.65 after 17 hours from the start of fermentation, and then gradually decreased to a final pH of 5.34. This means that the consumption of synthesis gas is reduced compared to autotrophic fermentation when the adsorption resin is not comprised because of inhibitory effect of hexanoic acid to the cells even if semi-mixotrophic fermentation is performed.

Example 1

The synthesis gas consumption and metabolite productivity of acetogen strains according to the semi-mixotrophic fermentation method of an embodiment of the present disclosure were analyzed according to the following method.

As the acetogen strain, *Clostridium* sp. JS66 was used.

As adsorption resins, TRILITE® GSH-20 (manufacturer: Samyang Corporation) and TRILITE® GSP-25 (manufacturer: Samyang Corporation) (hereinafter referred to as GSH 20 and GSP 25, respectively) were used.

First, the adsorption performances of the two adsorption resins were tested under microorganism-free conditions before applying them to fermentation. Per 1 liter of a total volume, 80 g of GSH 20, 1.5 g of ethanol, 1.5 g of butanol, 1.5 g of hexanol, 4 g of acetic acid, 2 g of butric acid, 4 g of hexanoic acid were added in a 15 ml conical tube, and the volume of the final solution was 5 ml. Likewise, per 1 liter of a total volume, 80 g of GSP 25, 1.5 g of ethanol, 1.5 g of butanol, 1.5 g of hexanol, 4 g of acetic acid, 2 g of butric acid, 4 g of hexanoic acid were added in a 15 ml conical tube, and the volume of the final solution was 5 ml. For the adsorption performance test, the solvent to which the adsorption resin, organic acid, and organic alcohol were added was distilled water, and the conical tube in which the adsorption resin, organic acid, and organic alcohol were added was subject to the adsorption reaction for 3 hours in a shaking incubator at 30° C. and 150 rpm. After the adsorption reaction, the adsorption resin and the solvent layer were separated, and the adsorbed organic acids and organic alcohols and the organic acids and organic alcohols remaining in the solution were analyzed. After the adsorption reaction, a process of recovering adsorbed ethanol, butanol, hexanol, acetic acid, butyric acid, and hexanoic acid was performed for each of the separated adsorption resins GSH 20 and GSP25. For the recovery process, 5 ml of ethyl acetate was added to each of the separated GSH 20 and GSP25, and then the recovery process was carried out for 3 hours in a shaking incubator at 30° C. and 150 rpm. An ethyl acetate-based solution containing the recovered product was analyzed. Ethanol, butanol, hexanol, acetic acid (AA), butyric acid (BA) and hexanoic acid (HA) were analyzed using a gas chromatography (Agilent Technologies 6890N, CA, USA) equipped with a flame ionization detector (FID). For the column, HP-Innowax (agilent, 30 m×0.32 mm×0.25 μm) was used, and the inlet temperature was maintained at 250° C. and the detector temperature was maintained at 250° C. The oven temperature was increased from an initial temperature of 50° C. to a final temperature of 250° C. in increments of 10° C./min. Helium gas was used as the moving gas and the inlet pressure was maintained at 9.41 psi.

Figure 3A:
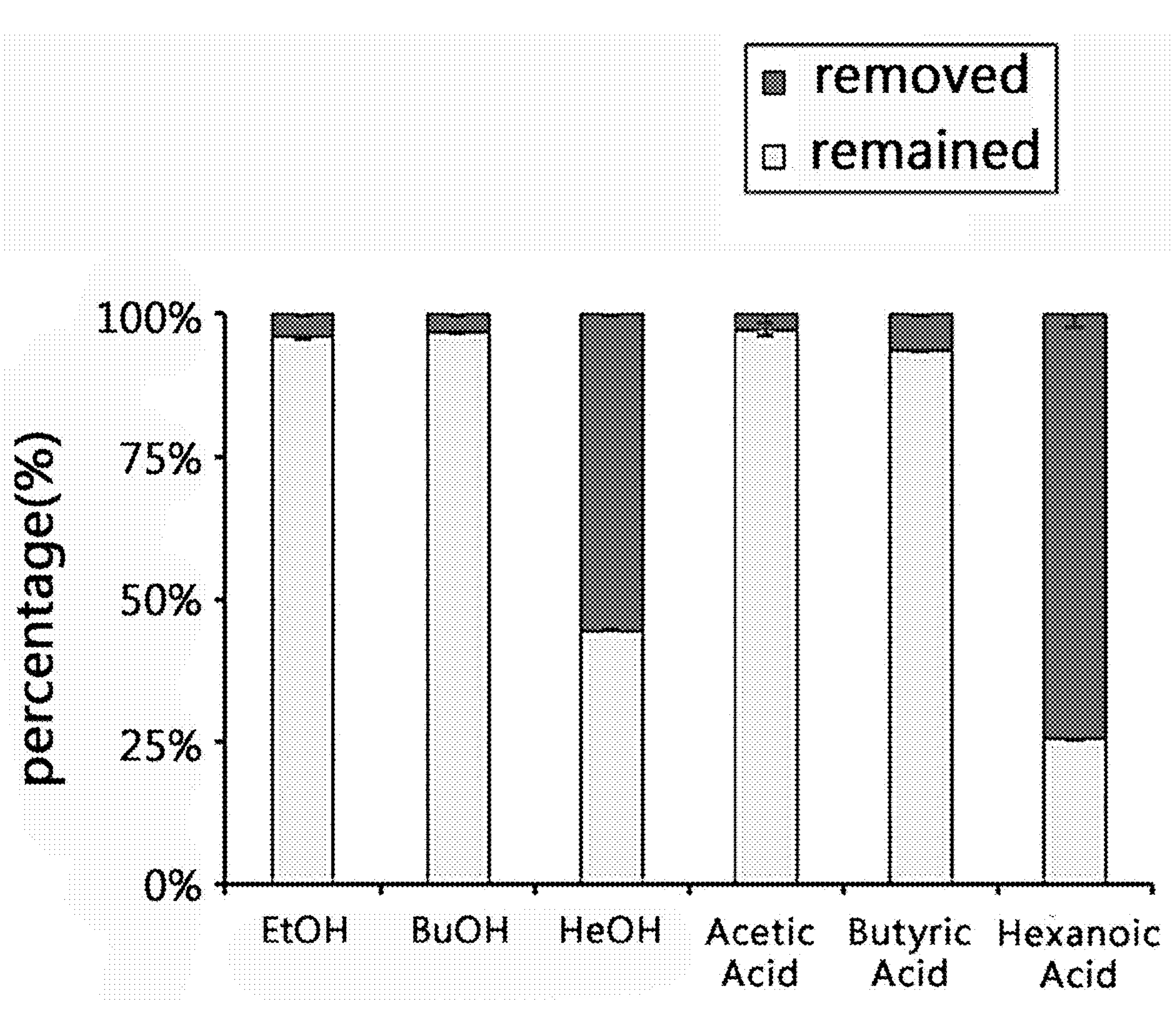
FIG. 3A is a diagram showing a removal rate of each compound of GSH 20, which is an adsorption resin used in one embodiment of the present disclosure.
Figure 3B:
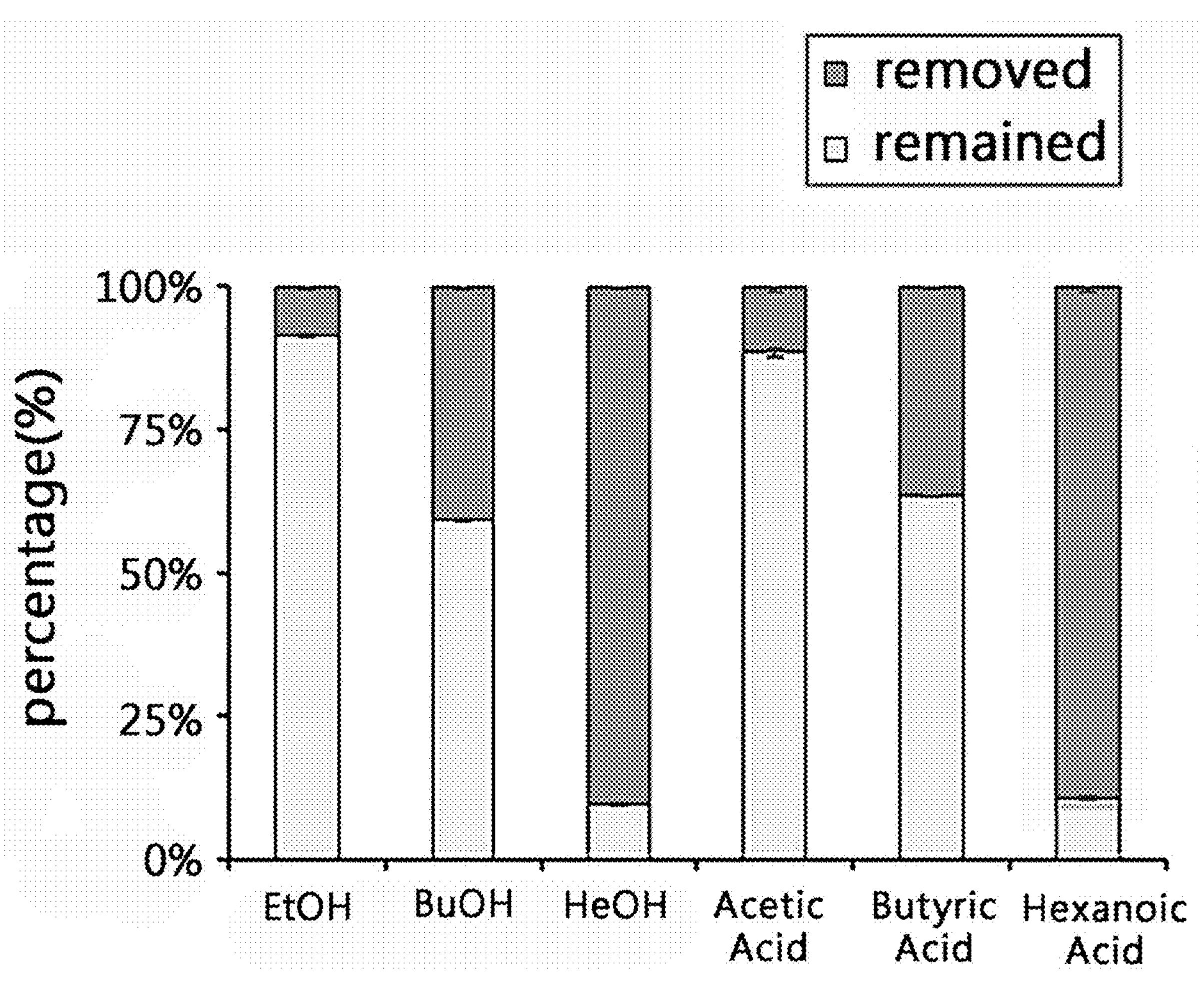
FIG. 3B is a diagram showing a removal rate of each compound of GSP 25, which is an adsorption resin used in one embodiment of the present disclosure.

As a result, the concentrations of ethanol, butanol, hexanol, acetic acid, butric acid, and hexanoic acid removed from GSH 20 were 0.06, 0.05, 0.87, 0.12, 0.12, and 2.75 g per 1 liter of a total volume, respectively. The concentrations of ethanol, butanol, hexanol, acetic acid, butric acid, and hexanoic acid removed in GSP 25 were 0.13, 0.64, 1.42, 0.48, 0.69 and 3.39 g per 1 liter of a total volume, respectively. FIG. 3A shows the removal rate of each compound removed from GSH 20. The removal rates of hexanol, hexanoic acid, and the remaining materials were 55%, 75%, and about 5%, respectively. FIG. 3B shows the removal rate of each compound removed from GSP 25. For alcohols and organic acids, the removal rates increased from 2 carbon compounds to 6 carbon compounds, and thus, the removal rates were increased to 10%, 40% and 90%. This means that GSH 20 and GSP 25 can remove hexanoic acid more selectively than other materials.

Based on the above results, semi-mixotrophic fermentation using the two adsorption resins was performed according to an embodiment of the present disclosure. The same medium as in Comparative Example 2 was used. In semi-mixotrophic fermentation, fermentation was initiated by adding glucose as carbon sources and synthesis gas at the beginning of fermentation. This step is a mixotrophic fermentation in which glucose and synthesis gas are present at the same time. After that, when all of the glucose in the same medium is consumed, no additional glucose is added and only synthesis gas is added in fed-batch culture. This step is an autotrophic fermentation in which only synthesis gas is present. In semi-mixotrophic fermentation, glucose exists only at the beginning of fermentation to increase cell mass, and then only synthesis gas is added to the same medium in fed-batch culture to increase gas substrate consumption, which is distinct from the method of re-adding both sugar and synthesis gas. After putting 20 ml of medium in a 157 ml serum bottle and inoculating microorganisms, synthesis gas was supplied at 1.25 bar. The adsorption resin for hexanoic acid removal was added at 1.6 g per 20 ml medium so that GSH20 and GSP25 were 80 g per 1 liter of a total volume, respectively. Synthesis gas was injected with carbon monoxide (CO), carbon dioxide ($CO_2$), and hydrogen ($H_2$) at a ratio of 3:3:4, respectively. The culture was performed at a rotational speed of 100 rpm at a temperature of 30° C. in a shaking incubator. The sugar in the medium was consumed within 24 hours, and even after the sugar in the medium was consumed, synthesis gas was continuously injected and further fermented for 341 hours, and the final fermentation time was 365 hours. After fermentation, a process of recovering adsorbed ethanol, butanol, hexanol, acetic acid, butyric acid, and hexanoic acid was performed for each of the separated adsorption resins GSH 20 and GSP25. For the recovery process, 20 ml of ethyl acetate was added to each of the separated GSH 20 and GSP25, and then the recovery process was carried out for 3 hours in a shaking incubator at 30° C. and 150 rpm. An ethyl acetate-based solution containing the recovered product was analyzed. Gas consumption, pH change, and production materials over time were analyzed in the same manner as in Comparative Example 1.

Figure 4A:
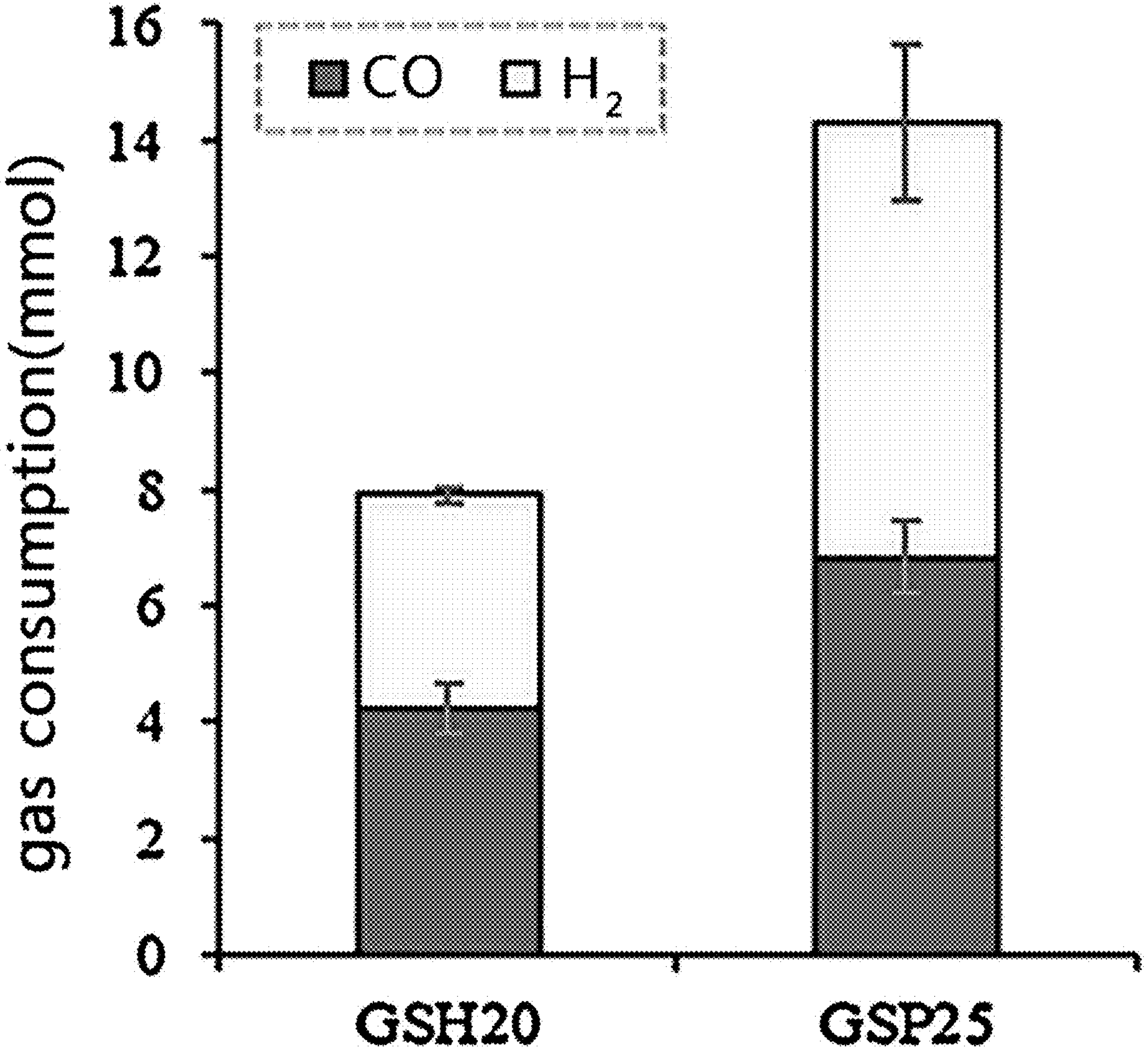
FIG. 4A is a diagram showing a total gas consumption of an acetogen strain for each adsorption resin and gas type in a method according to one embodiment of the present disclosure.

As a result, as shown in FIG. 4A, the total gas consumption was 7.9 mmol and 14.3 mmol, respectively, when GSH 20 and GSP25 were used as the adsorption resin, which was significantly higher than the result in Comparative Example 2 in which no adsorption resin was used. Also, the gas consumption was 81% higher when using GSP 25, compared to using GSH 20. The above result means that the utilization rate of synthesis gas increases according to the method according to an embodiment of the present disclosure.

Figure 4B:
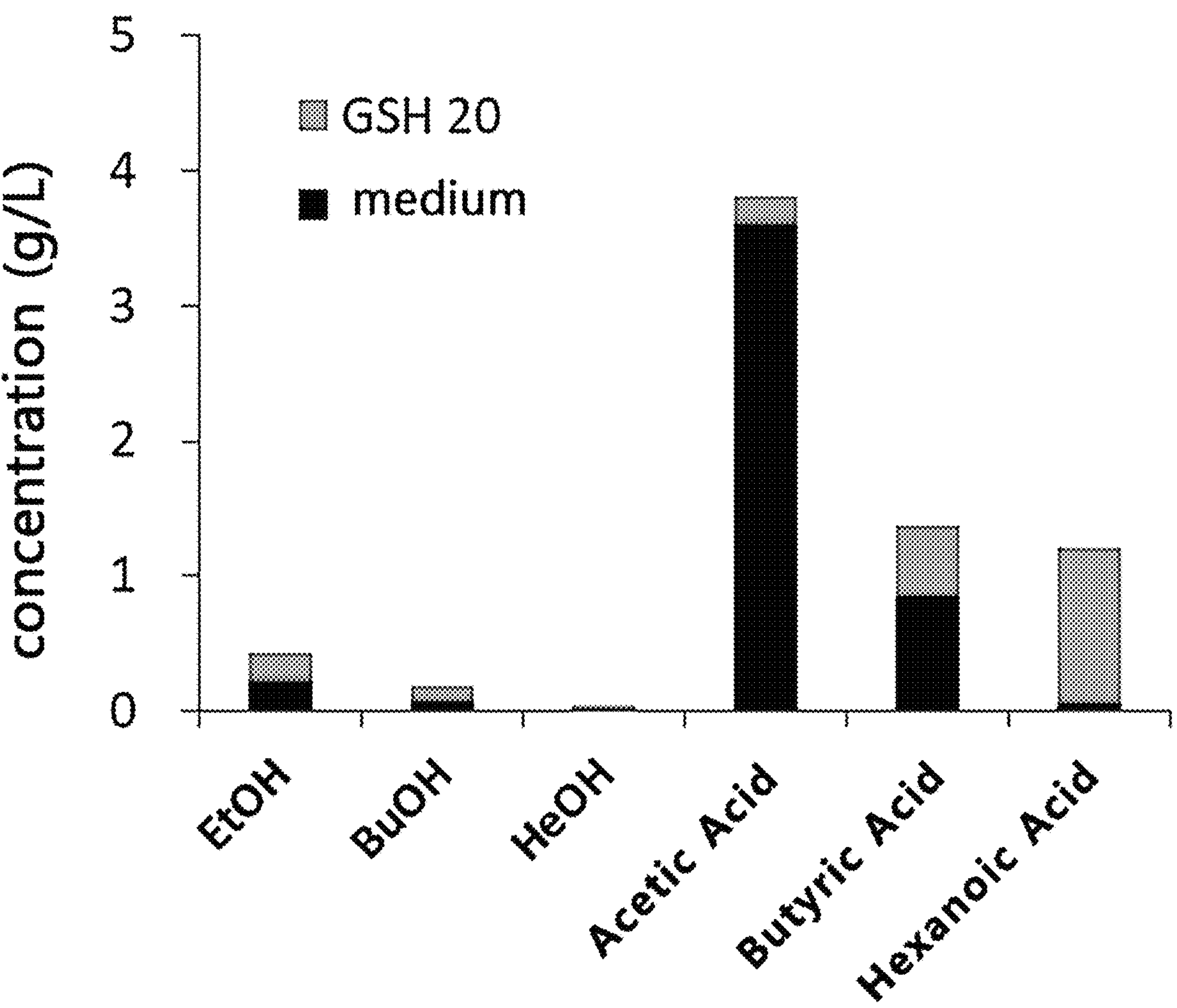
FIG. 4B is a diagram showing removed metabolites and non-removed metabolites in a culture medium for each compound when GSH 20 is used as an adsorption resin in a method according to one embodiment of the present disclosure.
Figure 4C:
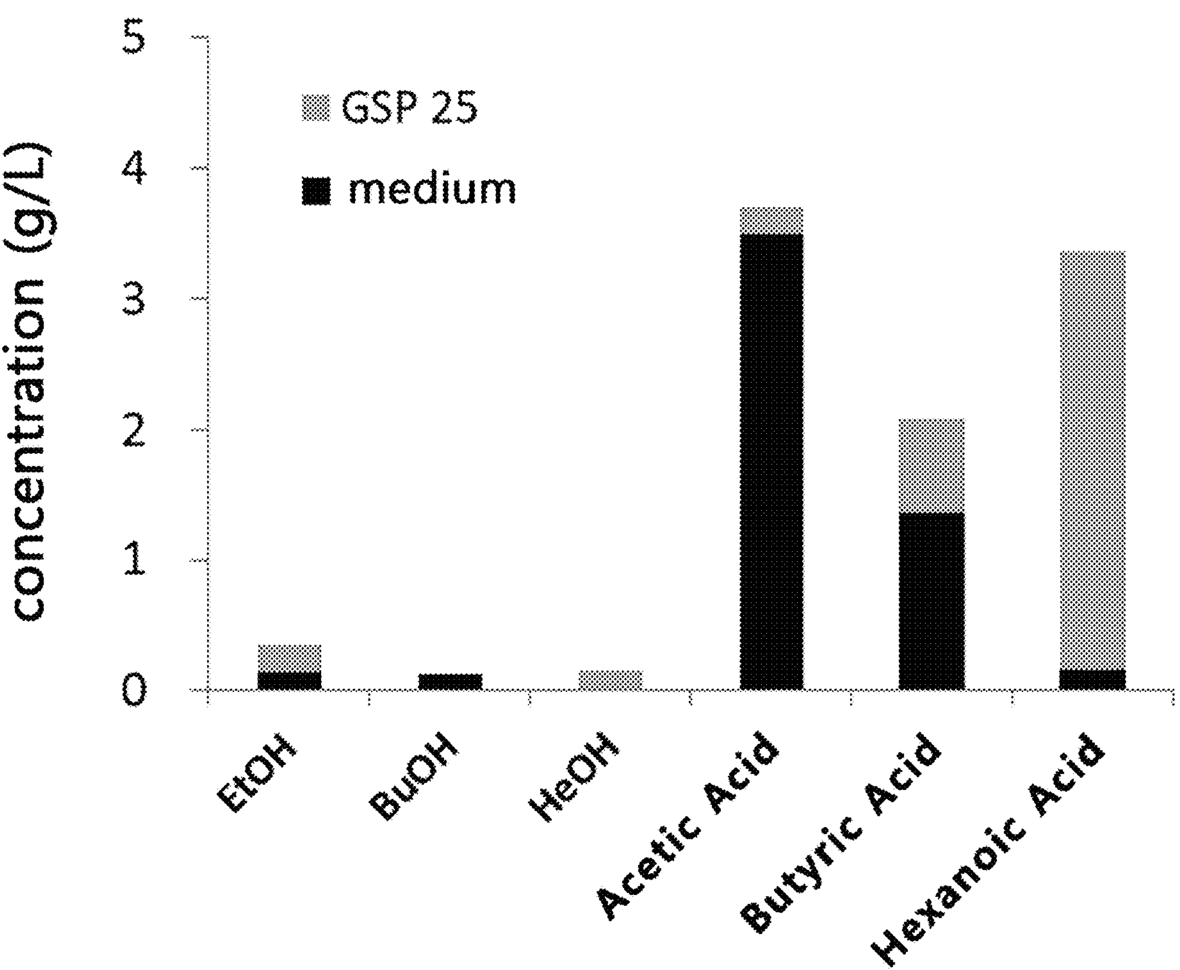
FIG. 4C is a diagram showing removed metabolites and non-removed metabolites in a culture medium for each compound when GSP 25 is used as an adsorption resin in a method according to one embodiment of the present disclosure.
Figure 4D:
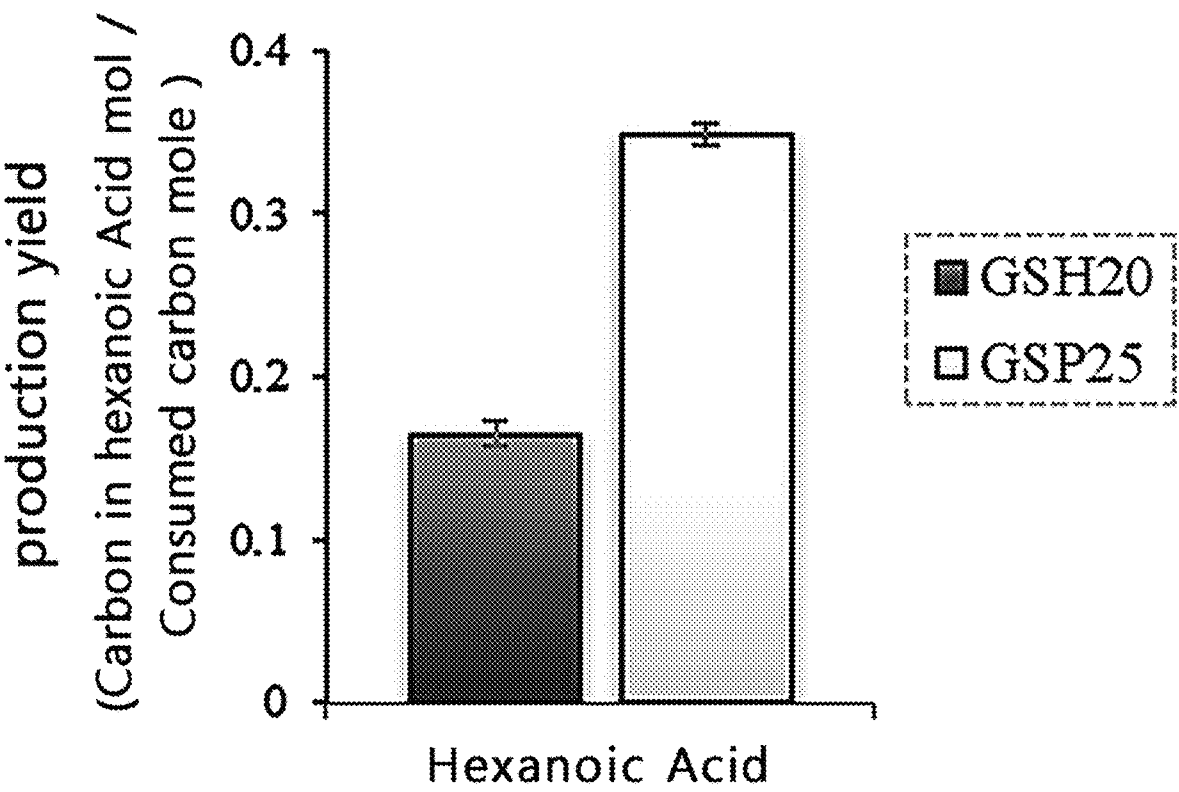
FIG. 4D is a diagram showing a yield of hexanoic acid produced by a method according to one embodiment of the present disclosure for each adsorption resin.
Figure 4E:
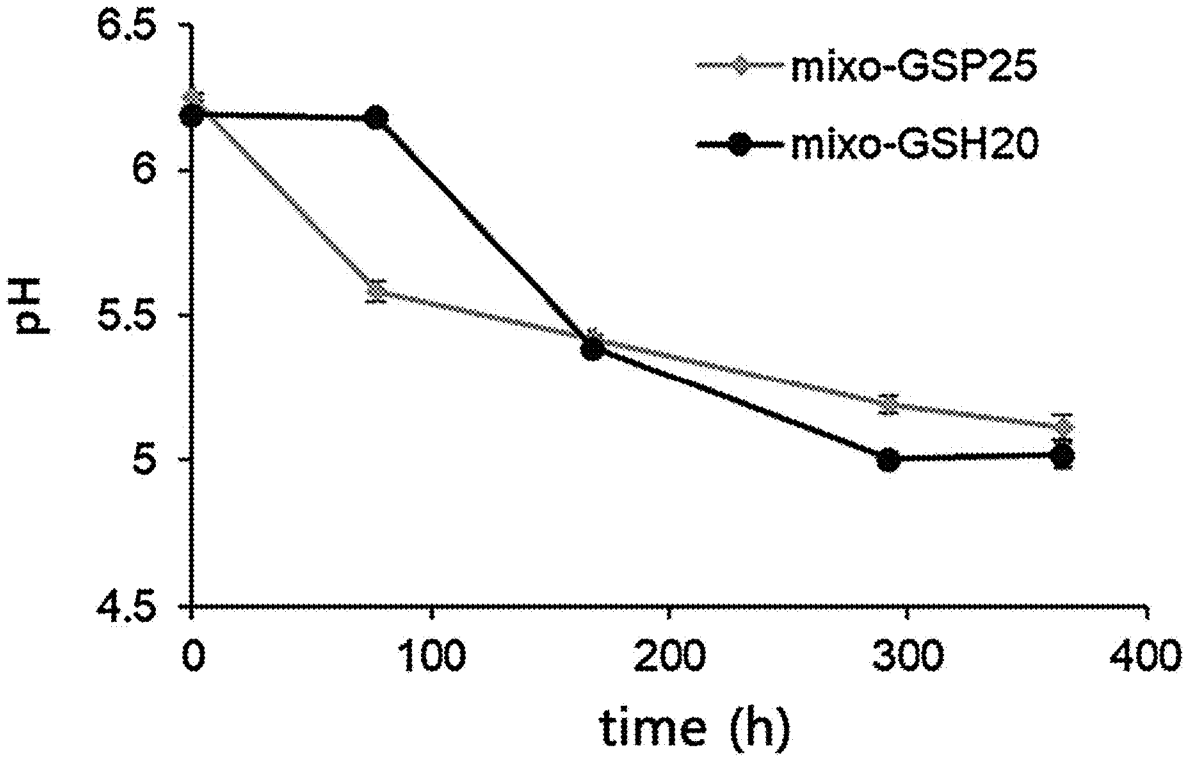
FIG. 4E is a diagram showing an analysis of pH change according to a fermentation time of an acetogen strain in a method according to one embodiment of the present disclosure.

In addition, as shown in FIGS. 4B to 4D, the concentration of hexanoic acid produced was 1.21 g and 3.37 g per 1 liter of a total volume, respectively, in the condition where GSH 20 and GSP25 were added. The concentration was 2.8 times higher when using GSP25 than when using GSH 20. This was found to be high compared to the result of Comparative Example 2 (FIG. 2B) in which the concentration of hexanoic acid produced was 1.16 g per 1 liter of a total volume when the adsorption resin was not used. Therefore, comparing the concentration of produced hexanoic acid in case of using the adsorption resin and in case of using no absorption resin, the production yield of hexanoic acid increased by 4.3% under the adsorption condition using GSH20 and by 190.5% under the adsorption condition using GSP25. FIG. 4E shows the analysis of pH change over time. In the semi-mixotrophic fermentation with the addition of GSP25, the pH decreased from 6.25 at the beginning to 5.58 after 77 hours, and then gradually decreased thereafter, resulting in a final pH of 5.11 at the end of fermentation. In the semi-mixotrophic fermentation with the addition of GSH20, the pH decreased from 6.19 at the beginning to 6.18 after 77 hours and then gradually decreased thereafter, resulting in a final pH of 5.02 at the end of fermentation. Therefore, although the degree of initial pH decrease is different in the above two cases, the final pH showed a similar pattern.

The above result means that according to the method according to an embodiment of the present disclosure, the yield of acetic acid decreases and the yield of hexanoic acid increases, thereby having excellent effects in improving synthesis gas consumption and hexanoic acid production.

Example 2

In the semi-mixotrophic fermentation method according to an embodiment of the present disclosure, the CO consumption and hexanoic acid production tendency of the acetogen strain according to the supply amount of carbon monoxide (CO) contained in the synthesis gas were analyzed by culturing *Clostridium* sp. JS66 in the same manner as in Example 1, except for the amount of carbon monoxide supplied in the synthesis gas composition in the second fermentation step. GSP 25 was used as the adsorption resin.

In the semi-mixotrophic fermentation according to an embodiment of the present disclosure, after consuming sugar at an early stage, the carbon and energy sources are supplied as synthesis gas, so the metabolites produced depend on the consumption of synthesis gas. For the production of hexanoic acid, chain extension from Acetyl-CoA to Hexanoyl-CoA is required, and NADH can provide reducing power for chain extension. Therefore, the experiment was conducted under the condition of increasing the proportion of carbon monoxide in the composition of the synthesis gas provided from 30% to 60%. The initial gas ratio was $CO:H_2:CO_2$ equal to 30:40:30, and the synthesis gas ratio added in the second fermentation step was 30:40:30 or 60:30:10.

Figure 5A:
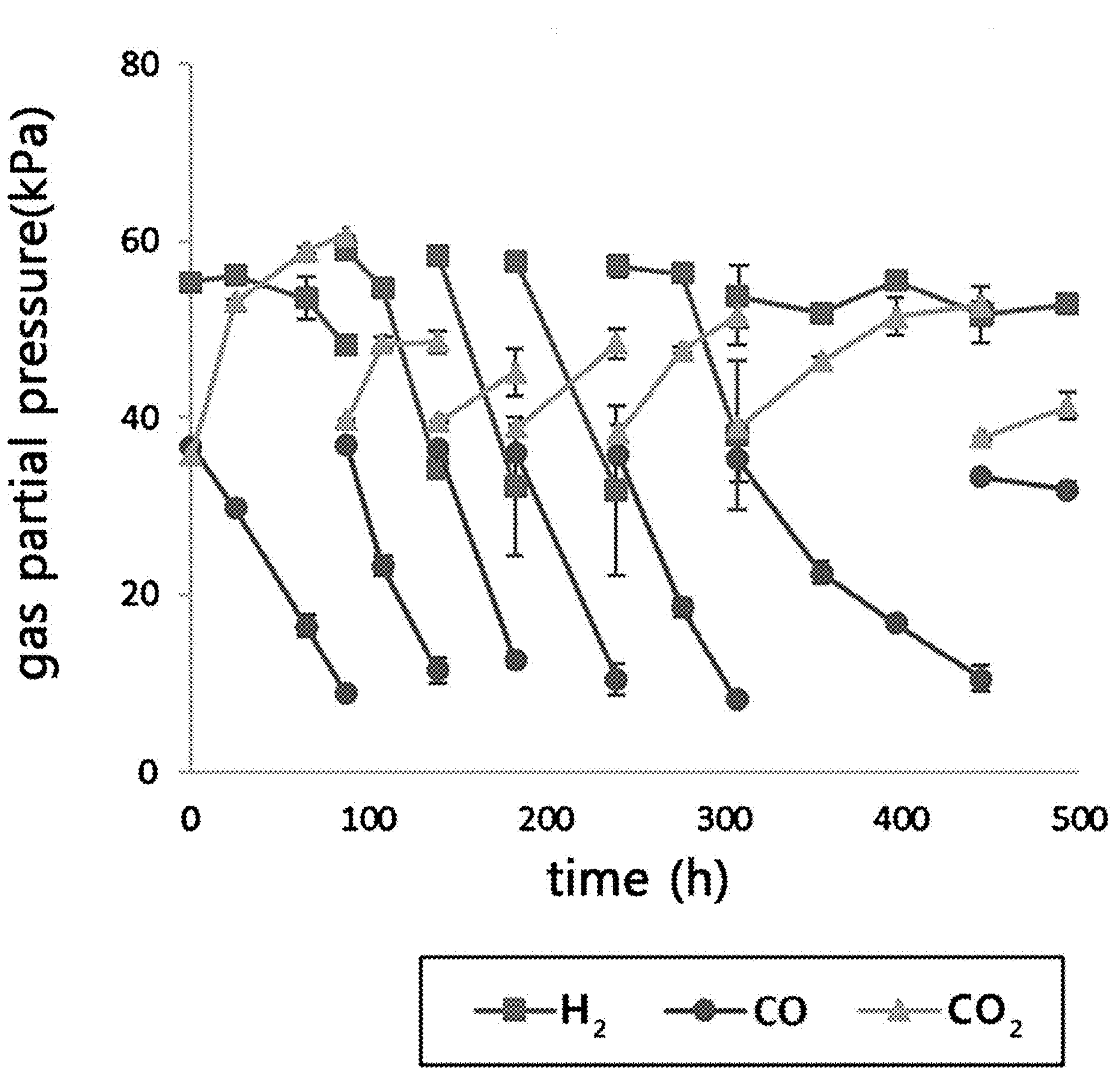
FIG. 5A is a diagram showing a result of analyzing CO consumption of an acetogen strain according to CO supply amount (CO 30%) in a method according to one embodiment of the present disclosure.
Figure 5B:
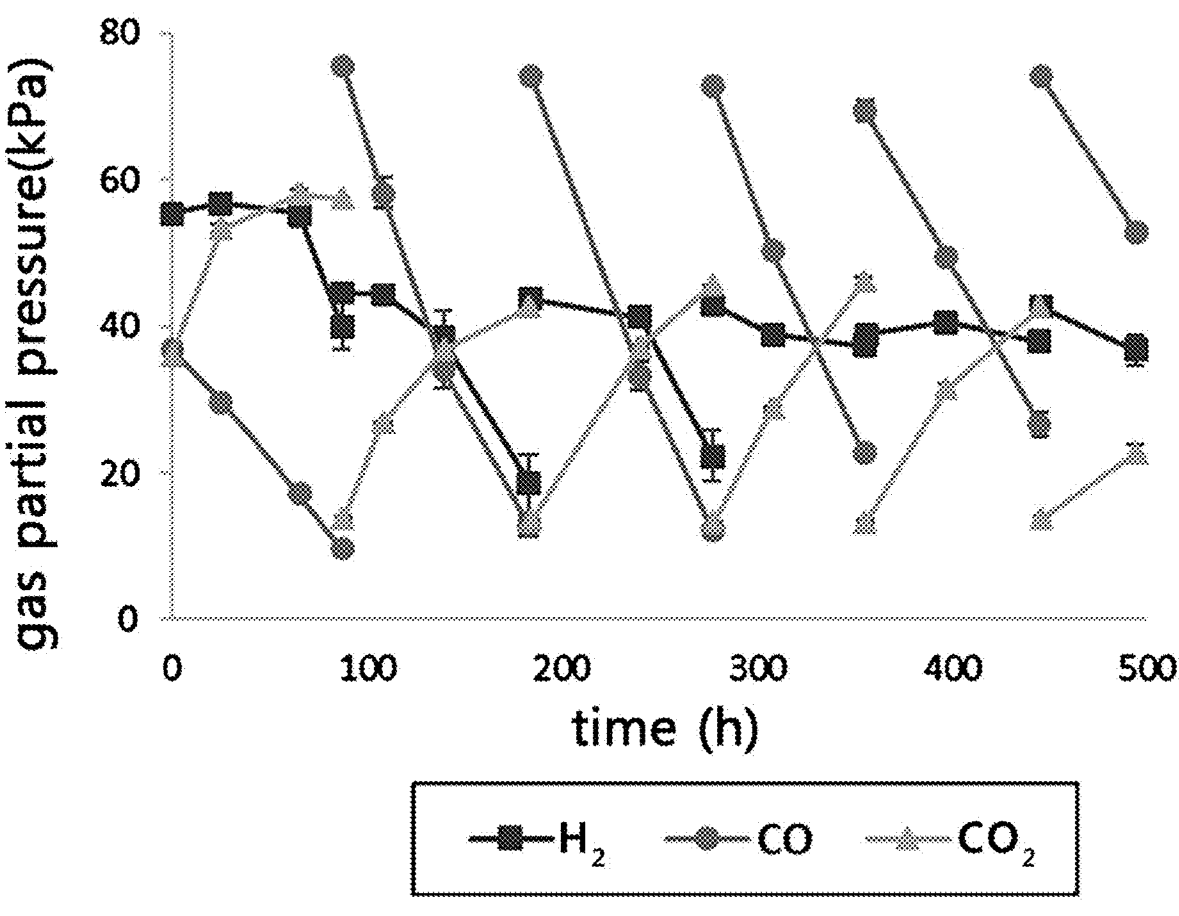
FIG. 5B is a diagram showing a result of analyzing CO consumption of an acetogen strain according to CO supply amount (CO 60%) in a method according to one embodiment of the present disclosure.
Figure 5C:
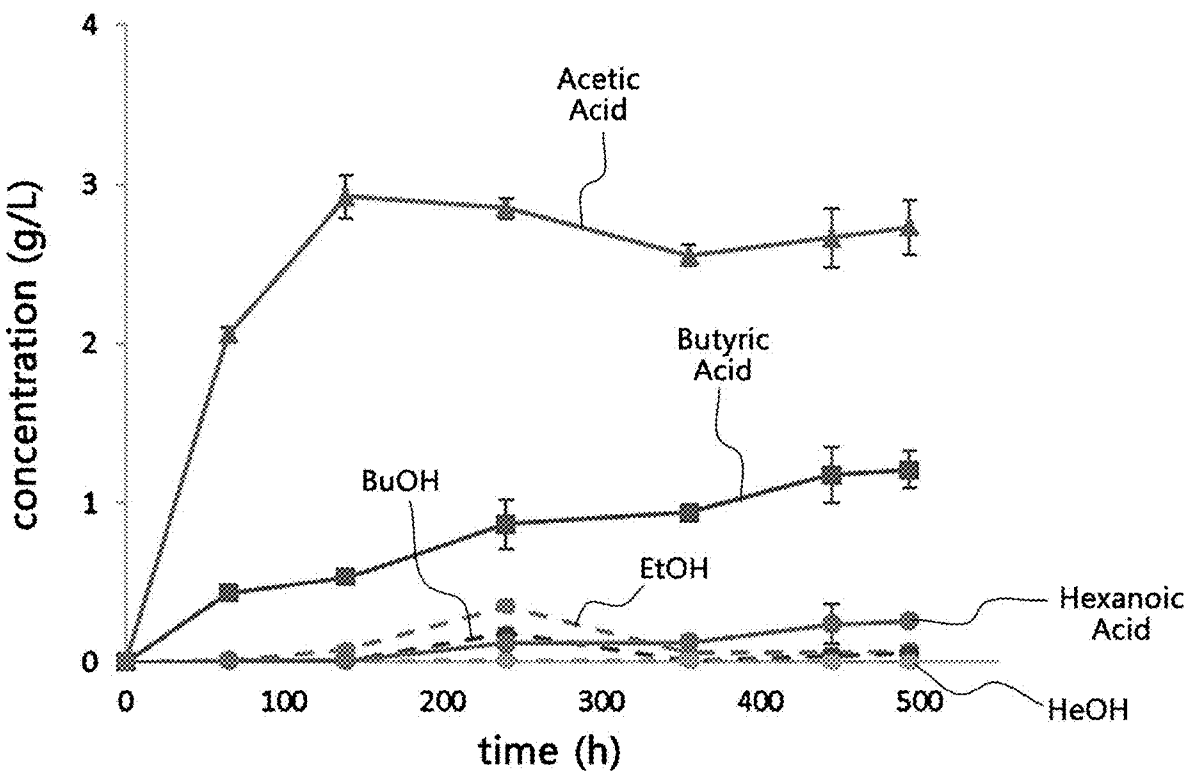
FIG. 5C is a diagram showing metabolites remaining in a medium that are not removed from an adsorption resin for each compound according to an amount of CO supplied (CO 30%) in a method according to an embodiment of the present disclosure.
Figure 5D:
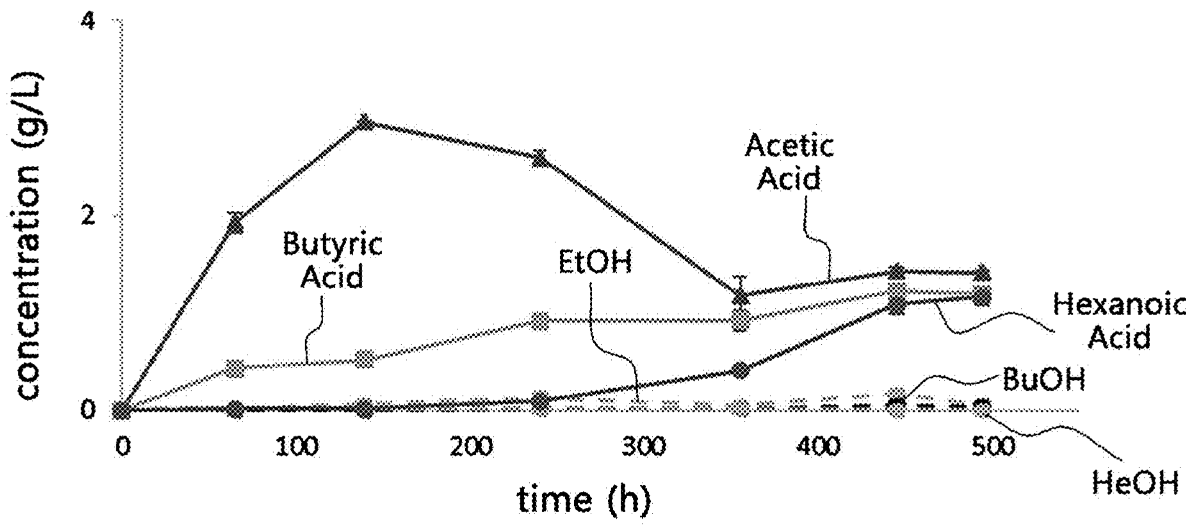
FIG. 5D is a diagram showing metabolites remaining in a medium that are not removed from an adsorption resin for each compound according to an amount of CO supplied (CO 60%) in a method according to an embodiment of the present disclosure.
Figure 5E:
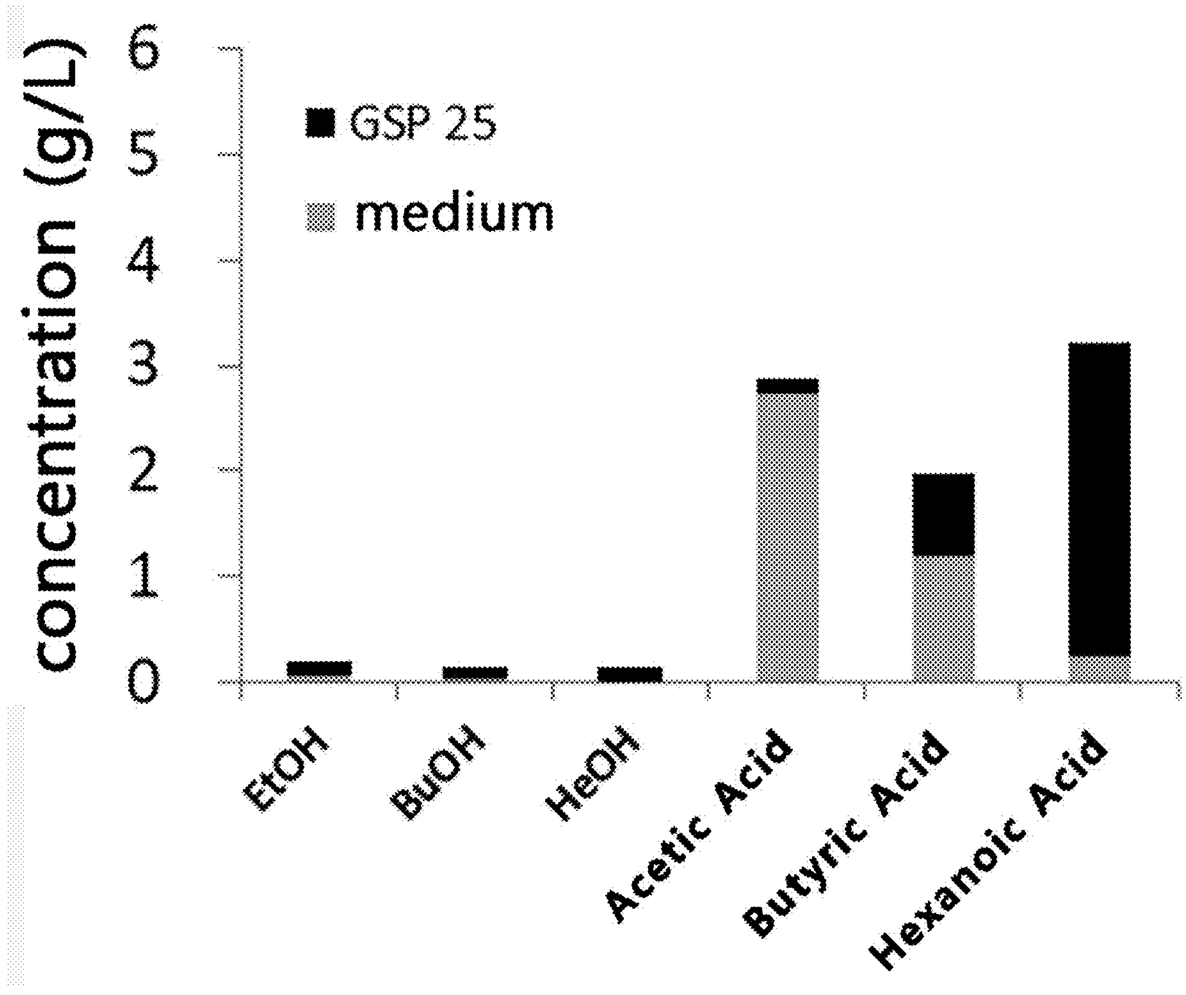
FIG. 5E is a diagram showing concentrations of metabolites removed and concentrations of metabolites that are not removed and present in a culture medium for each compound when an adsorption resin GSP25 is used according to an amount of CO supplied (CO 30%) in a method according to an embodiment of the present disclosure.
Figure 5F:
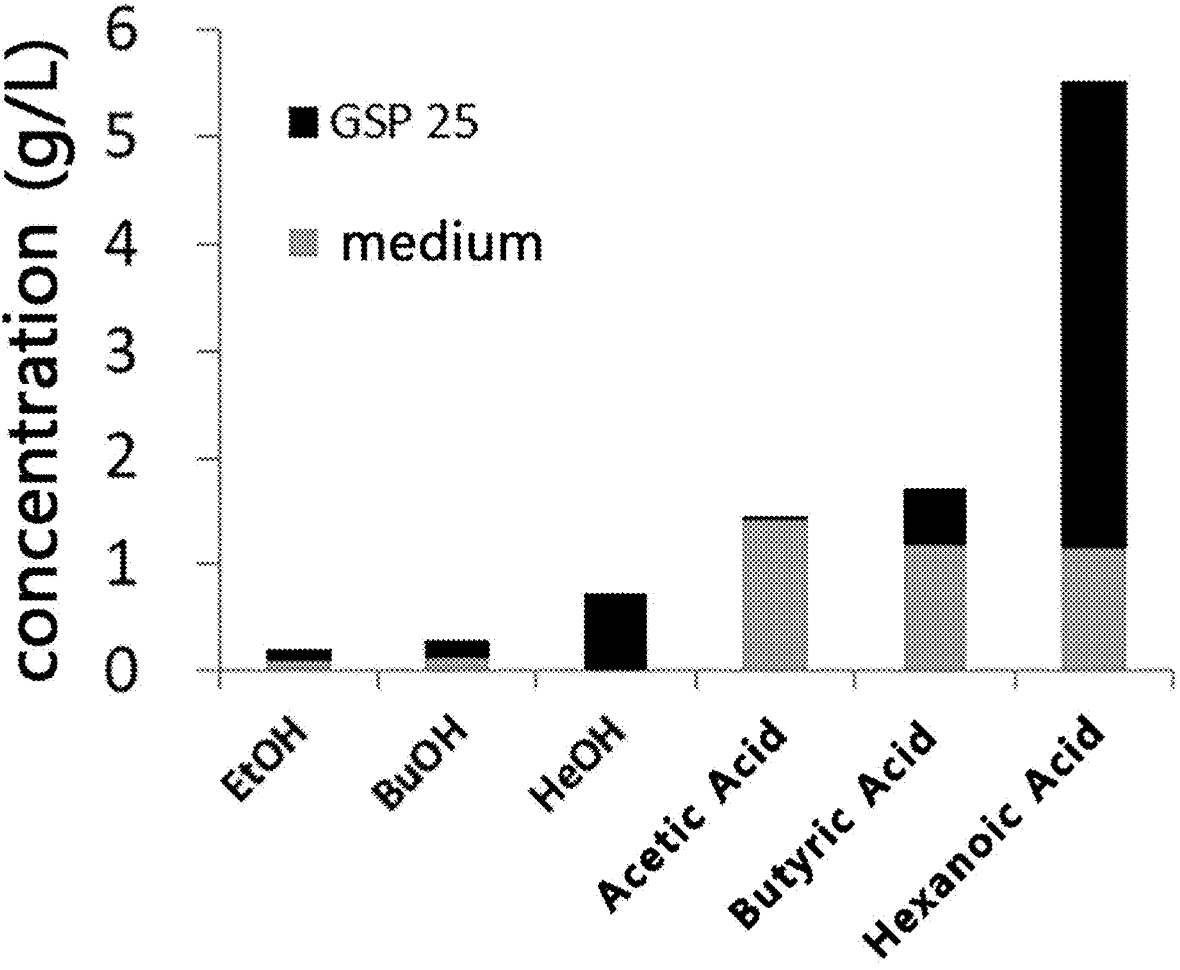
FIG. 5F is a diagram showing concentrations of metabolites removed and concentrations of metabolites that are not removed and present in a culture medium for each compound when an adsorption resin GSP25 is used according to an amount of CO supplied (CO 60%) in a method according to an embodiment of the present disclosure.

As a result, the total gas consumptions of hydrogen and carbon monoxide were 14 and 18 mmol based on the number of moles of carbon under the conditions of 30% and 60% carbon monoxide, respectively, and among them, the consumptions of carbon monoxide were 8.3 and 14.2 mmol, respectively. Thus, as the amount of carbon monoxide provided increased, the amount of carbon monoxide consumed increased (FIGS. 5A and 5B).

Figure 6:
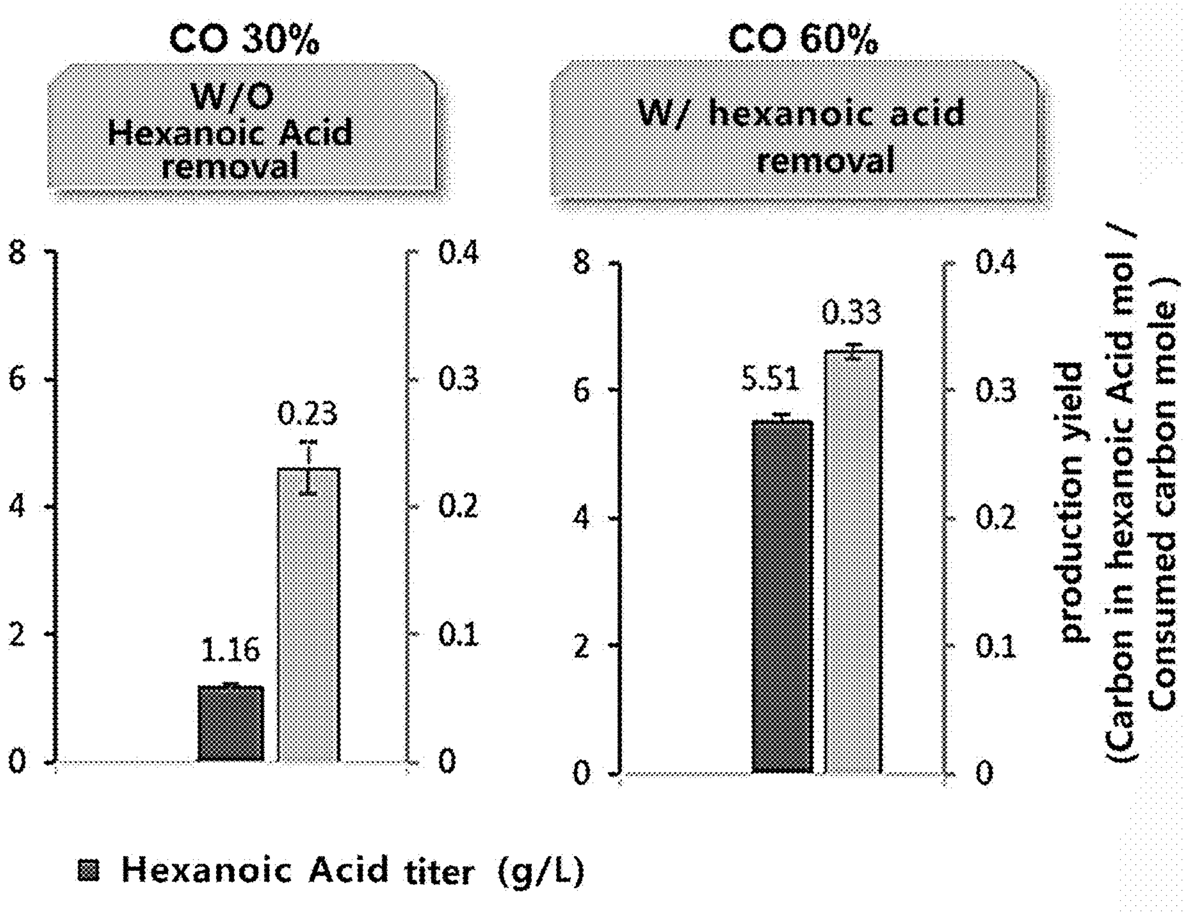
FIG. 6 is a diagram showing a comparison of titer and yield of hexanoic acid in case where hexanoic acid is not removed from a medium by performing fermentation without an adsorption resin while supplying 30% CO and in case where hexanoic acid is removed from a medium by performing fermentation with an adsorption resin GSP25 while supplying 60% CO in a method according to an embodiment of the present disclosure.

It was noticeable in the residual product remaining in the medium without being removed by GSP25 is that the concentration of hexanoic acid increases as the concentration of acetic acid decreases after 250 hours, the latter half of fermentation under the condition of 60% carbon monoxide. The final concentrations of the hexanoic acid produced, which were obtained by summing the residual in the medium and the ones extracted in the adsorbent resin, were 3.2 and 5.5 g per 1 liter of a total volume under the conditions of 30% and 60% carbon monoxide, respectively (FIG. 5C to FIG. 5F). In terms of yield, as the amount of added carbon monoxide increased, the yields of acetic acid and butric acid decreased and the yield of hexanoic acid increased (FIG. 6). That is, the increase in NADH production due to the increase in carbon monoxide consumption means that hexanoic acid production was increased by providing sufficient reducing power for chain extension.

Example 3

In order to confirm whether the method according to an embodiment of the present disclosure can be used for other acetogen strains, the autotrophic fermentation was performed in the same medium as in Comparative Example 1 in the same way except that *Clostridium carboxidivorans* P7 (ATCC BAA-624) was used and carbon monoxide was injected as a carbon source.

Figure 7A:
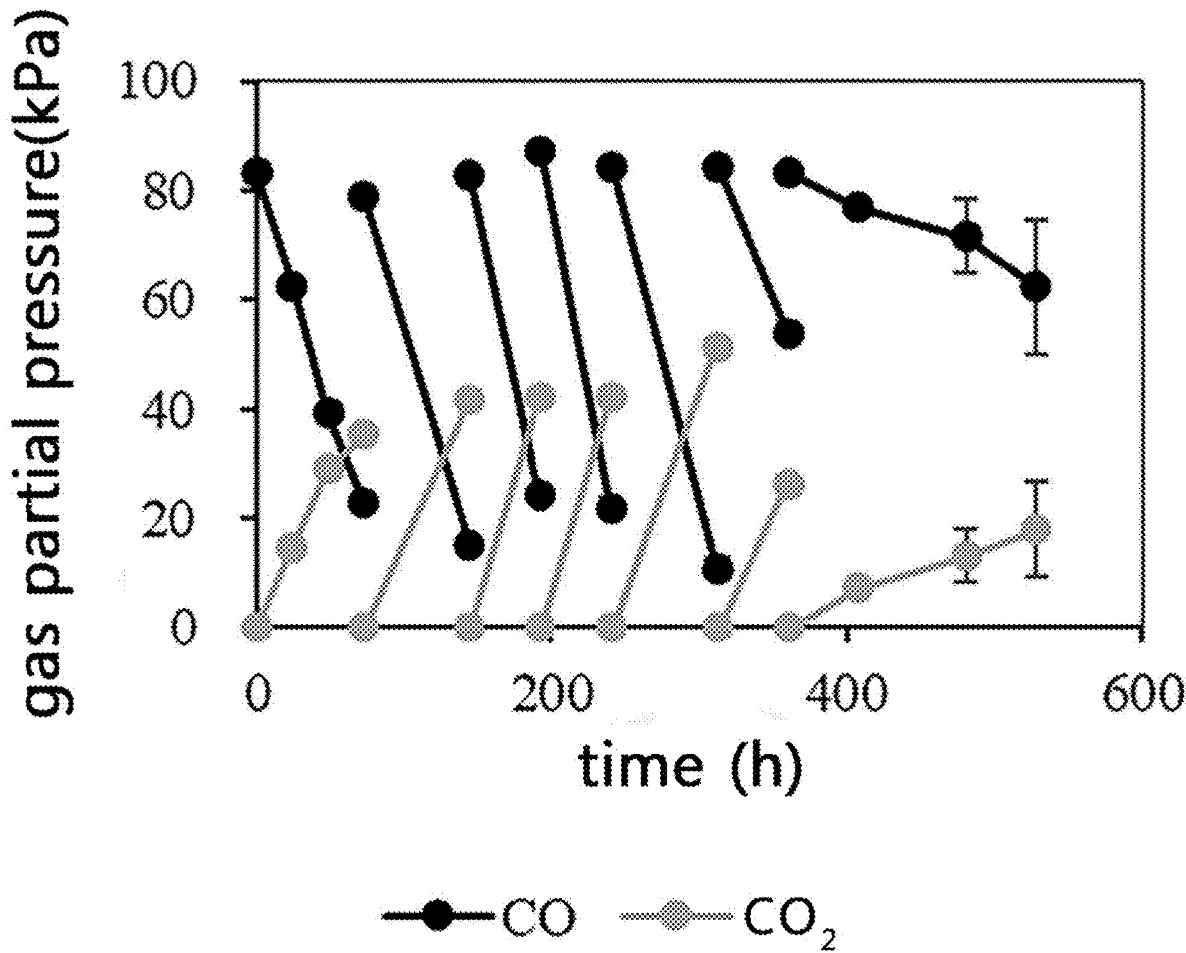
FIG. 7A is a diagram showing a total gas consumption when a fermentation was performed using *Clostridium carboxydiborans* P7 as an acetogen strain in Example 3 of the present disclosure.
Figure 7B:
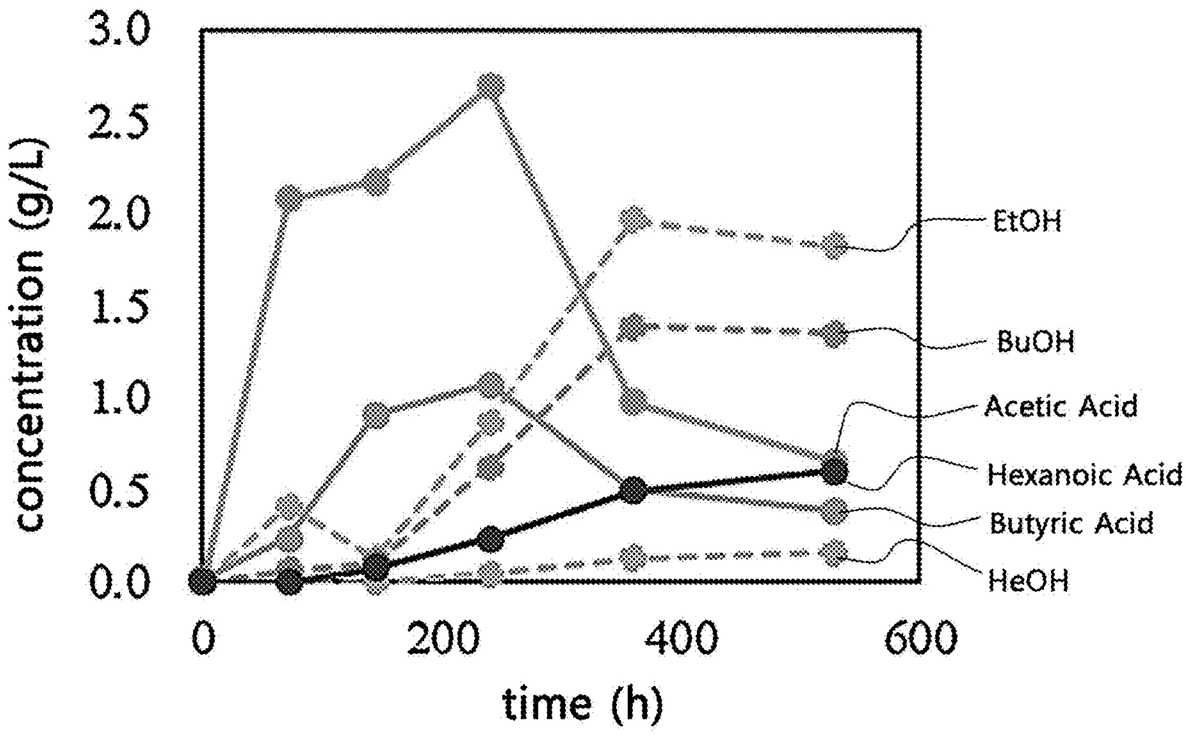
FIG. 7B is a diagram showing concentrations of metabolites remaining in a medium when a fermentation was performed using *Clostridium carboxidivorans* P7 as an acetogen strain in Example 3 of the present disclosure.
Figure 7C:
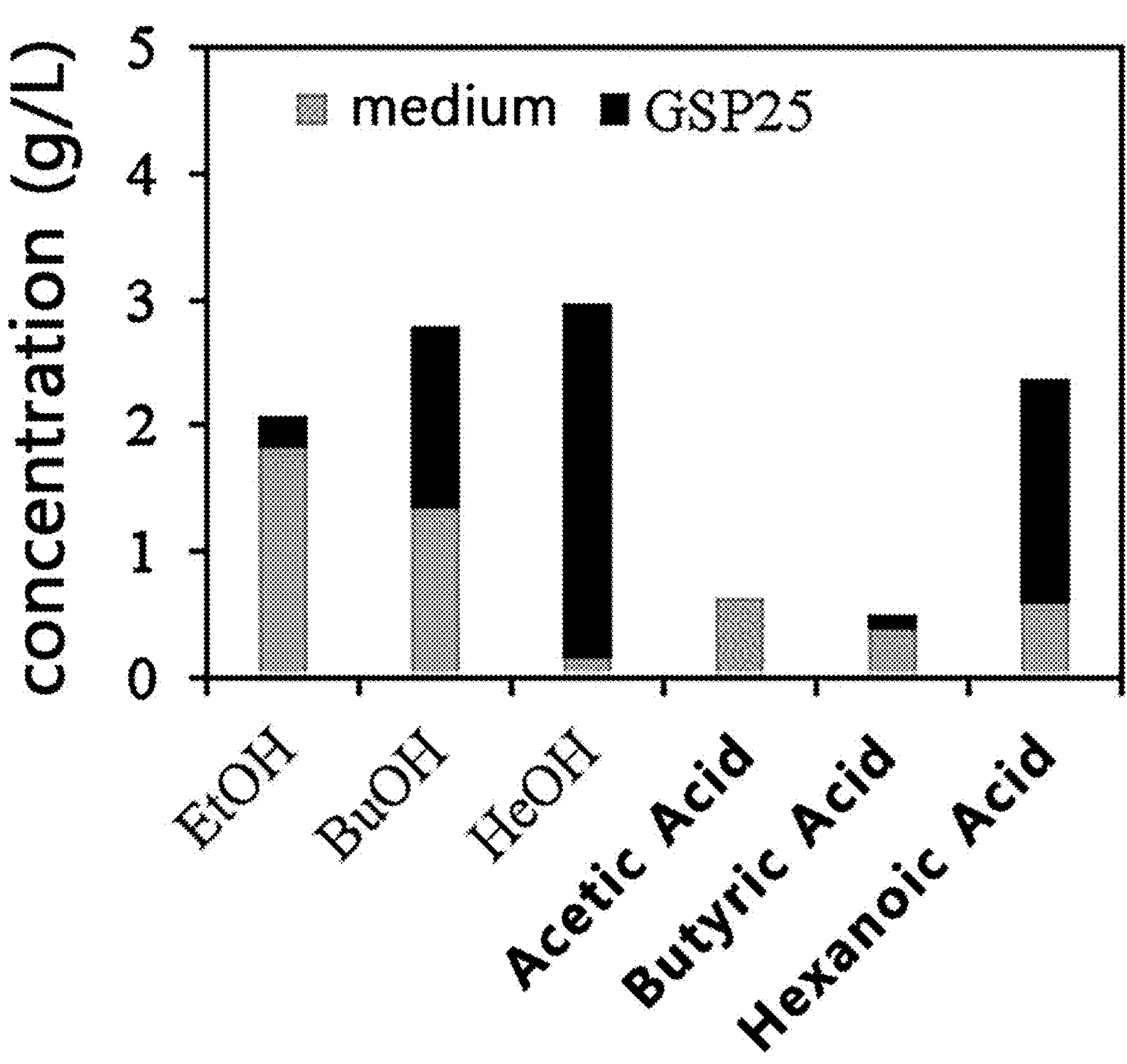
FIG. 7C is a diagram showing concentrations of metabolites removed and metabolites present in a culture medium without being removed when a fermentation was performed with GSP25 as an adsorption resin and *Clostridium carboxidivorans* P7 as an acetogen strain in Example 3 of the present disclosure.

As a result, gas was consumed for 528 hours during fermentation, and the total gas consumption was 13.75 mmol of carbon monoxide (FIG. 7A). Regarding the concentration of metabolites remaining in the medium, acetic acid decreased after 240 hours, and ethanol and butanol increased (FIG. 7B). As final metabolites, hexanol and hexanoic acid were produced at 2.96 and 2.39 g/L, respectively, of which 94.93% and 74.89% were adsorbed to the adsorption resin (FIG. 7C). The above result means that *Clostridium carboxidivorans* P7 can be used as an acetogen strain in the method according to an embodiment of the present disclosure.

The present disclosure may provide the following embodiments as one embodiment.

First embodiment may provide a method for producing a metabolite using an acetogen strain, comprising:

a first fermentation step of fermenting an acetogen strain in a medium comprising synthesis gas and sugar;

a second fermentation step of further fermenting the cultured acetogen strain by supplying the synthesis gas in the same medium after all the sugars are consumed in the first fermentation step, wherein the medium further comprises an adsorption resin of a metabolite, and the metabolite comprises a carbon number of C2 to C6.

Second embodiment may provide the method of the first embodiment, wherein the synthesis gas comprised in each medium of the first fermentation step and the second fermentation step comprises at least one of carbon monoxide, carbon dioxide and hydrogen.

Third embodiment may provide the method of the first or second embodiment, wherein the carbon monoxide in the synthesis gas is comprised in 40 to 100 pressure % based on a total pressure of the synthesis gas.

Forth embodiment may provide the method of any one of the first to third embodiments, wherein the sugar comprised in the medium of the first fermentation step comprises at least one of glucose, fructose, galactose, xylose, arabinose, mannose, cellobiose, and sucreose.

Fifth embodiment may provide the method of any one of the first to fourth embodiments, wherein the adsorption resin comprises porous polymer particles.

Sixth embodiment may provide the method of any one of the first to fifth embodiments, wherein the porous polymer particles satisfy one or more of the followings: a specific surface area of 700 to 1500 m 2/g; a pore radius of 40 to 85 Å; a particle size range of 200 to 1500 μm; and a pore volume of 0.8 to 1.8 ml/g.

Seventh embodiment may provide the method of any one of the first to sixth embodiments, wherein the porous polymer particles are porous aromatic-based polymer particles.

Eighth embodiment may provide the method of any one of the first to seventh embodiments, further comprising the step of recovering the metabolite from the adsorption resin after the second step fermentation.

Ninth embodiment may provide the method of any one of the first to eighth embodiments, wherein the acetogen strain is a *Clostridium* sp. strain.

Tenth embodiment may provide the method of any one of the first to ninth embodiments, wherein the metabolite comprises one or more of hexanoic acid, hexanol, butyric acid and butanol.

Eleventh embodiment may provide the method of any one of the first to tenth embodiments, wherein the method produces the hexanoic acid by converting 25 mol % or more of a total carbon mole (C mol) of consumed carbon source to a carbon mole (C mol) of the hexanoic acid.

What is claimed is:

1. A method for producing hexanoic acid using a *Clostridium* sp. strain, the method comprising:

a first fermentation step of fermenting the *Clostridium* sp. strain in a medium comprising synthesis gas and sugar;

a second fermentation step of further fermenting the *Clostridium* sp. strain by supplying the synthesis gas in the same medium after all the sugars are consumed in the first fermentation step, wherein the medium further comprises an adsorption resin comprising porous polymer particles having a specific surface area of 700 to 1500 $m^2/g$, a pore radius of 40 to 85 Å, a particle size range of 200 to 1500 μm, and a pore volume of 0.8 to 1.8 ml/g.

2. The method of claim 1, wherein the synthesis gas comprised in each medium of the first fermentation step and the second fermentation step comprises at least one of carbon monoxide, carbon dioxide and hydrogen.

3. The method of claim 2, wherein carbon monoxide in the synthesis gas is comprised in 40 to 100 pressure % based on a total pressure of the synthesis gas.

4. The method of claim 1, wherein the sugar comprised in the medium of the first fermentation step comprises at least one of glucose, fructose, galactose, xylose, arabinose, mannose, cellobiose, and sucrose.

5. The method of claim 1, wherein the porous polymer particles are porous aromatic-based polymer particles.

6. The method of claim 1, further comprising a step of recovering the hexanoic acid from the adsorption resin after the second step fermentation.

7. The method of claim 1, wherein the *Clostridium* sp. strain is a *Clostridium* sp. JS66 or *Clostridium carboxidivorans* P7.

8. The method of claim 1, wherein the method produces the hexanoic acid by converting 25 mol % or more of a total carbon mole (C mol) of consumed carbon source to a carbon mole (C mol) of the hexanoic acid.

* * * * *